United States Patent
Abell et al.

(10) Patent No.: US 9,108,978 B2
(45) Date of Patent: Aug. 18, 2015

(54) ANTIMICROBIAL COMPOUNDS

(71) Applicants: ADELAIDE RESEARCH & INNOVATION PTY LTD, Adelaide (AU); MONASH UNIVERSITY, Clayton (AU)

(72) Inventors: Andrew Abell, Dulwich (AU); Steven Polyak, Payneham (AU); Grant Booker, Glenalta (AU); John Wallace, North Adelaide (AU); Tatiana Soares da Costa, Hawthorn (AU); Angie Jarrad, Panorama (AU); William Tieu, Findon (AU); Kelly Lee Keeling, Eden Hills (AU); Daniel Sejer Pedersen, Valby (DK); Nicole Pendini, Clayton (AU); Matthew Wilce, Wheelers Hill (AU); Min Yin Yap, Wheelers Hill (AU)

(73) Assignees: Monash University, Clayton (AU); Adelaide Research & Innovation Pty Ltd, Adelaide (AU)

( * ) Notice: Subject to any disclaimer, the term of this patent is extended or adjusted under 35 U.S.C. 154(b) by 0 days.

(21) Appl. No.: 14/346,646

(22) PCT Filed: Sep. 21, 2012

(86) PCT No.: PCT/AU2012/001138
§ 371 (c)(1),
(2) Date: Mar. 21, 2014

(87) PCT Pub. No.: WO2013/040647
PCT Pub. Date: Mar. 28, 2013

(65) Prior Publication Data
US 2014/0296177 A1  Oct. 2, 2014

(30) Foreign Application Priority Data
Sep. 23, 2011 (AU) .................................. 2011903946
Sep. 26, 2011 (AU) .................................. 2011903957

(51) Int. Cl.
C07D 495/04 (2006.01)
C07F 9/6561 (2006.01)
C07H 19/20 (2006.01)
C07H 19/167 (2006.01)

(52) U.S. Cl.
CPC ............ *C07D 495/04* (2013.01); *C07F 9/6561* (2013.01); *C07F 9/65616* (2013.01); *C07H 19/167* (2013.01)

(58) Field of Classification Search
CPC ... A61K 31/00; C07F 9/6561; C07F 9/65616; C07H 19/167
USPC ............... 514/47, 263.24, 364, 383, 388, 81; 536/26.7; 544/277; 548/113, 131, 143, 548/255, 266.4, 303.7
See application file for complete search history.

(56) References Cited

U.S. PATENT DOCUMENTS

2008/0233163 A1* 9/2008 Assaf .......................... 424/422

FOREIGN PATENT DOCUMENTS

WO   WO-2006/056007   6/2006
WO   WO-2009/062241   5/2009

OTHER PUBLICATIONS

The Merck Manual, 1992, 16th Ed., pp. 100, 110 and 225.*
Soares Da Costa, et al. "Selective inhibition of Biotin Protein Ligase from *Staphylococcus aureus*", Journal of Biological Chemistry, 2012, 287(21), 17823-17832.

* cited by examiner

*Primary Examiner* — Ganapathy Krishnan
(74) *Attorney, Agent, or Firm* — Cesari and McKenna, LLP

(57) ABSTRACT

A new class of biotin protein ligase (BPL) inhibitors that have antibacterial activity against multiple *Staphylococcus aureus* isolates, including clinically important methicillin-resistant *S. aureus* (MRSA) are disclosed that are non-toxic.

6 Claims, 7 Drawing Sheets

6.09

ANTIMICROBIAL COMPOUNDS

CROSS-REFERENCE TO RELATED APPLICATIONS

This application is the National Stage of International Application No. PCT/AU2012/001138 filed on Sep. 21, 2012, which claims the benefit of Australian Patent Application No. 2011903946 filed on Sep. 23, 2011, and Australian Patent Application No. 2011903957 filed on Sep. 26, 2011. The contents of each application are hereby incorporated by reference in their entirety.

PRIORITY CLAIM

This international patent application claims priority from Australian provisional patent application 2011903946 filed 23 Sep. 2011 and Australian provisional patent application 2011903957 filed 26 Sep. 2011, the contents of both are incorporated by reference.

FIELD OF THE INVENTION

This invention relates to new biotin derivatives having potent BPL inhibition activity.

BACKGROUND

Bacteraemia is a constant threat to modern society and represents a significant burden to the healthcare system. In Australia alone it is estimated that there are 200,000 episodes of hospital-acquired infections each year, accounting for up to 2 million bed days in hospital. Patients who develop infections remain in hospital three times longer than other patients, resulting in additional costs and a lack of available beds for alternative uses. A significant number of these patients (estimated at 12,000 per year in healthcare) go onto develop blood stream infections. Of these 17-29% will die whilst in hospital, primarily due to ineffective treatment options. *Staphylococcus aureus* is the most important of these pathogens with a 20% mortality rate by 30 days. The ability to become pathogenic on entering the blood stream results in life-threatening bone and joint infections, endocarditis, pneumonia and septicaemia. Although the public profile of serious staphylococcal infections is that they are hospital-acquired, it is important to recognise that 60% of serious *S. aureus* infections are now thought to begin in the community.

Conventional antibiotic treatment for *S. aureus* infections utilises penicillinase-resistant penicillin. However, resistance to this agent is now prevalent in Australian hospital-associated strains and community-associated strains. Multidrug resistant strains, such as the hospital strains of methicillin-resistant *S. aureus* (MRSA), are also now present in most Australian hospitals and vancomycin-intermediate *S. Aureus* (VISA) strains are starting to emerge. A survey of Australian hospitals in 2005-06 revealed 24% of all *S. aureus* isolates were MRSA. Strains not susceptible to vancomycin (considered the last line of defence) pose a particular clinical problem, because there are very few agents available to treat them, and those that do exist (such as linezolid) have notable toxicity. Furthermore, the efficacy of vancomycin against vancomycin susceptible strains of MRSA is thought to be suboptimal. All this equates to a patient with MRSA infection costing a hospital five times more than one with methicillin-sensitive *S. aureus* infection.

There is a need to replenish the drug-discovery pipeline with new antibiotics to combat drug-resistant bacteria, including *Staphylococcus aureus*, which are responsible for a huge and growing health care problem Biotin Protein Ligase (BPL) is an essential enzyme found in all living organisms. BPL attaches the prosthetic group biotin (Vitamin H) onto a class of enzymes known as the biotin-dependent carboxylases. These enzymes play essential roles in metabolic reactions such as membrane biogenesis; a key process in all living organisms. As the attachment of a biotin prosthetic group is absolutely required for normal enzyme function, inhibition of BPL activity can be used to inhibit cell growth.

Given the essential role of BPLs in all organisms, inhibitors of the BPL enzyme from a pathogen would provide opportunities for either selective or broad-spectrum treatments for a range of non-viral infectious diseases.

Patent application WO 2009/062241 describes the crystal structure of the *S. aureus* biotin protein ligase and its use to identify molecules that interact with the biotin binding domain of the enzyme. WO 2006/056007 describes methods for the identification of BPL inhibitors.

However, neither of these documents discloses inhibitors of BPL.

It has now been surprisingly found that a certain class of compounds inhibit the essential metabolic enzyme BPL, and their structure is described in this patent application.

An object of the present invention is to provide a novel class of antibiotics.

A further object of the invention is to provide a novel class of antibiotic that are selective for a particular bacterial target.

Yet a further object of the present invention is to provide a novel class of antibiotic that are selectively imported into bacterial cells but not mammalian cells.

It is an object of the present invention to overcome, or at least substantially ameliorate, the disadvantages and shortcomings of the prior art.

Other objects and advantages of the present invention will become apparent from the following description, taking in connection with the accompanying drawings, wherein, by way of illustration and example, an embodiment of the present invention is disclosed.

SUMMARY OF THE INVENTION

The present invention relates to a compound of formula (I)

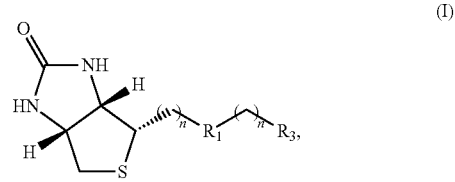

wherein
n is an integer from 1 to 10;
R₁ is selected from the group consisting of:
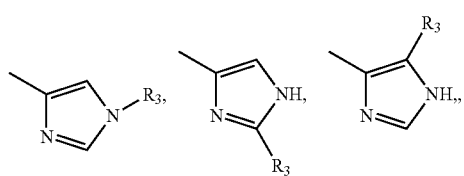
imidazole,
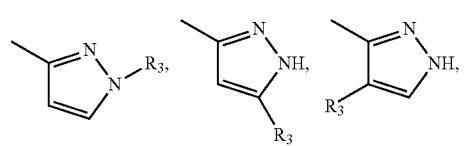
pyrazole,
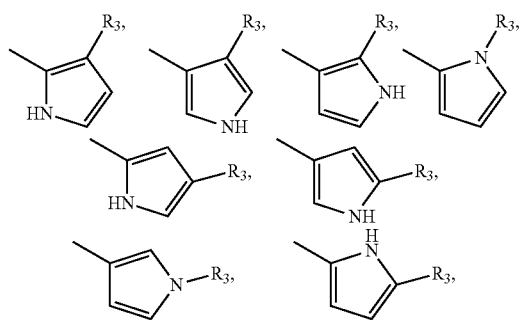
pyrrole,
thiophene,
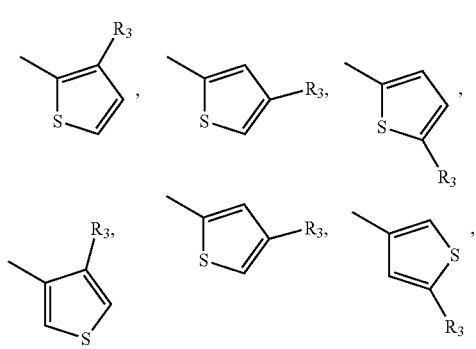
tetrazole,
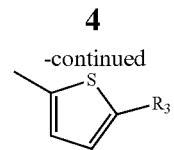
oxazole,
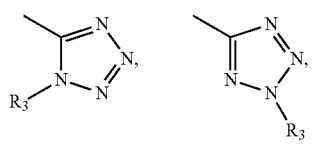
triazole
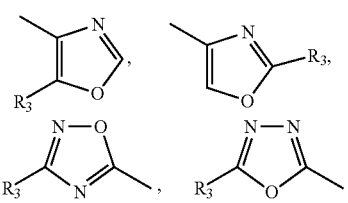
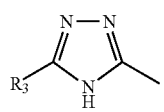
where X is selected from H or OH,
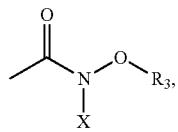
phosphodiester,
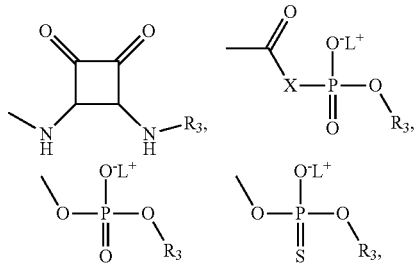

where L is selected from Na$^+$, K$^+$;

X is selected from CH$_2$, CF$_2$, NH,

R$_3$ is selected from the group consisting of:
  H, C$_1$-C$_{10}$ alkyl, C$_1$-C$_{10}$ alkenyl, C$_1$-C$_{10}$ alkynyl;
  a nucleoside, such as, but not limited to adenosine, cytidine, uridine, guanosine, thymidine, or inosine;
  adenine, guanine, thymine, uracil, cytosine;
  benzoxazolone, benzoxazole, benzofuran, benzimidazole,

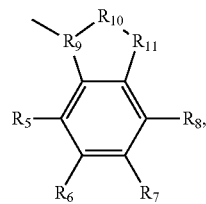

where:

R$_5$, R$_6$, R$_7$, R$_8$ are selected from the group consisting of H, C$_1$-C$_5$ alkyl, halogen, NH$_2$, OH$_2$, NR$_{12}$R$_{13}$, SH, SR$_{13}$:
  where R$_{12}$ and R$_{13}$ are selected from the group consisting of H, C$_1$-C$_5$ alkyl;

R$_9$ is selected from the group consisting of N, NH;

R$_{10}$ is selected from the group consisting of CH$_2$, C=O, C=N—R;

R$_{11}$ is selected from the group consisting of N, NH, O, S;

napthyl,

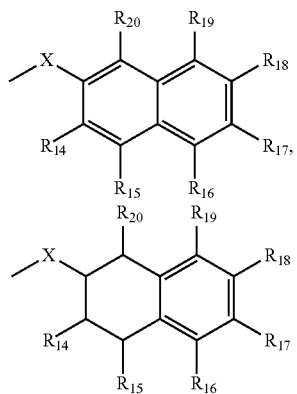

where:

X is selected from the group consisting of O, NR$_{12}$R$_{13}$, SR$_{13}$;

R$_{14}$, R$_{15}$, R$_{16}$, R$_{17}$, R$_{18}$, R$_{19}$, R$_{20}$ are selected from the group consisting of H, C$_1$-C$_5$ alkyl, halogen, NH$_2$, OH$_2$, NR$_{12}$R$_{13}$, SH, SR$_{13}$:
  where R$_{12}$ and R$_{13}$ are selected from the group consisting of H, C$_1$-C$_5$ alkyl.

In preference, a pharmaceutical composition including as an active ingredient at least one compound of formula (I) optionally together with one or more pharmacologically acceptable excipients.

In preference, the pharmaceutical composition when used for the treatment of infection selected from the group consisting of bacterial, fungal or protozoan infections.

Use of at least one compound according to formula (I) as an active ingredient in the preparation of a medicament for the treatment and/or prevention of bacterial infections, fungal infections, protozoan infections, The challenge for this approach is to develop inhibitors that target the pathogen without harm to the host. These compounds are termed "differential inhibitors". Research has demonstrated that significant differences do exist in the BPLs of different organisms including the molecular mass, amino acid sequences and kinetic properties. It is these differences that will be exploited in the discovery and development of differential inhibitors.

FIGURES

Figure 3A:
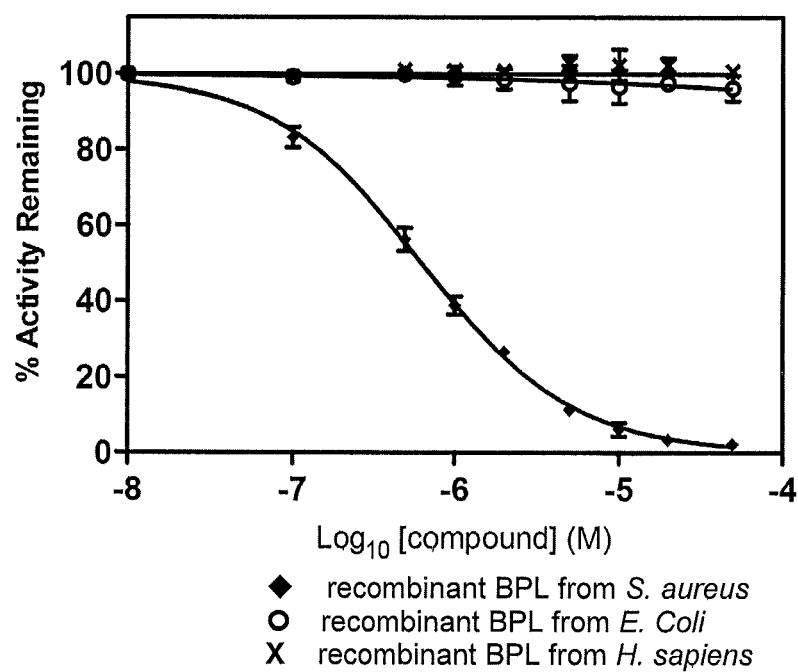
Figure 3B:
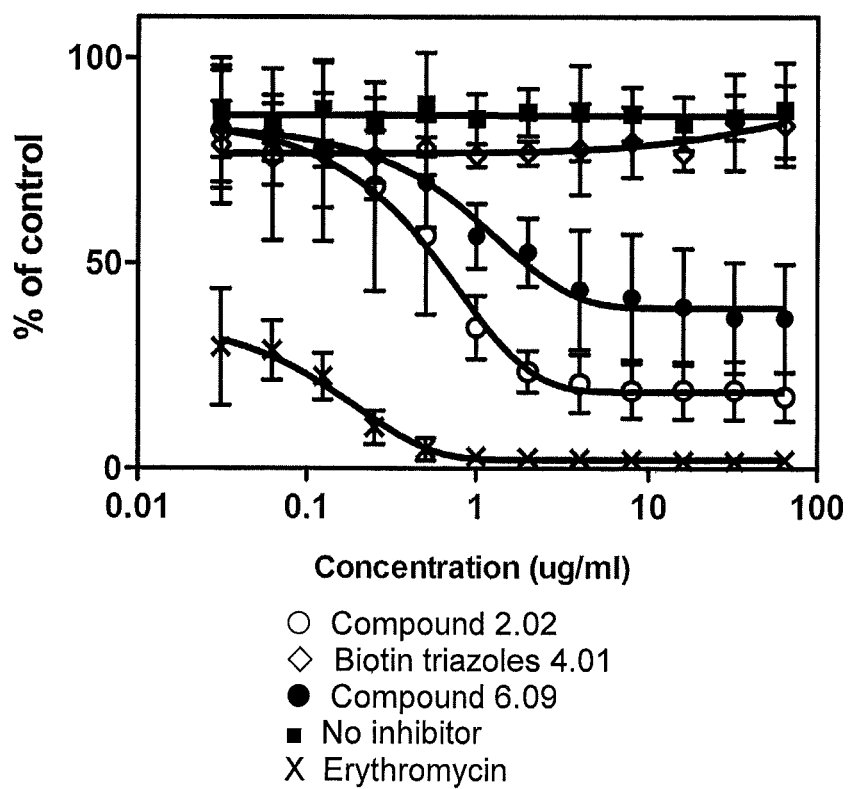
Figure 3C:
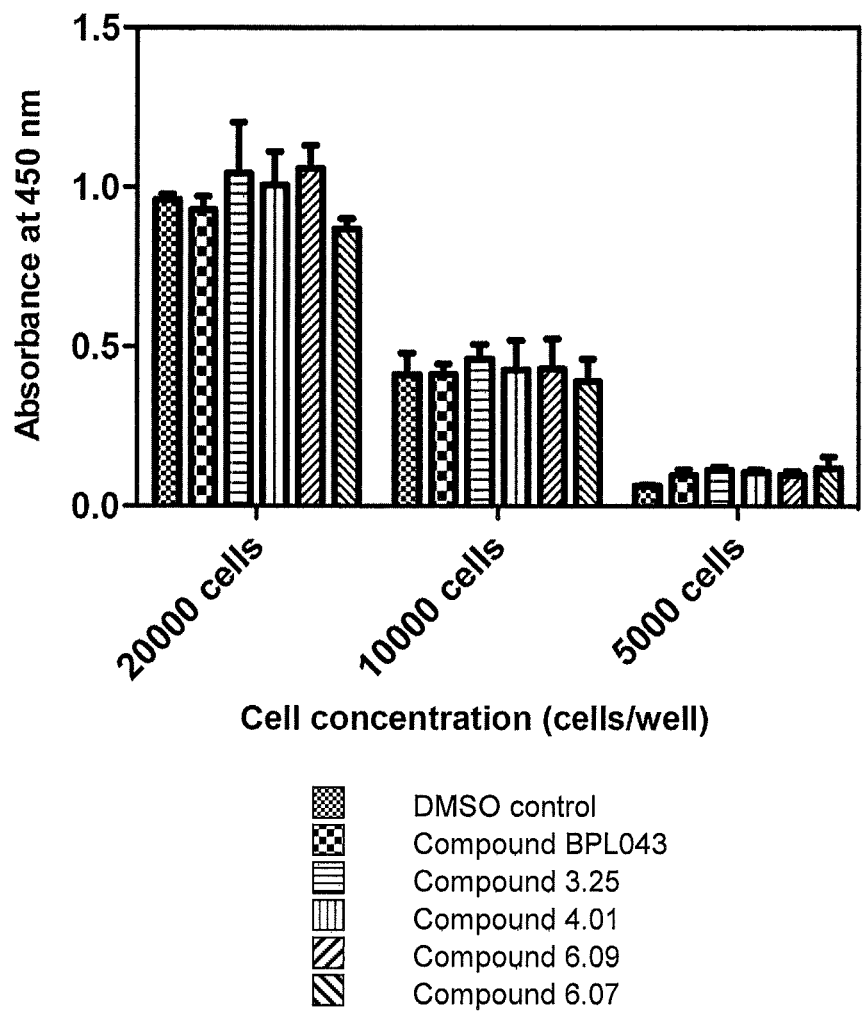

FIG. 3*a*-3*c* shows biological data of biotin triazole BPL inhibitors

Figure 4A:
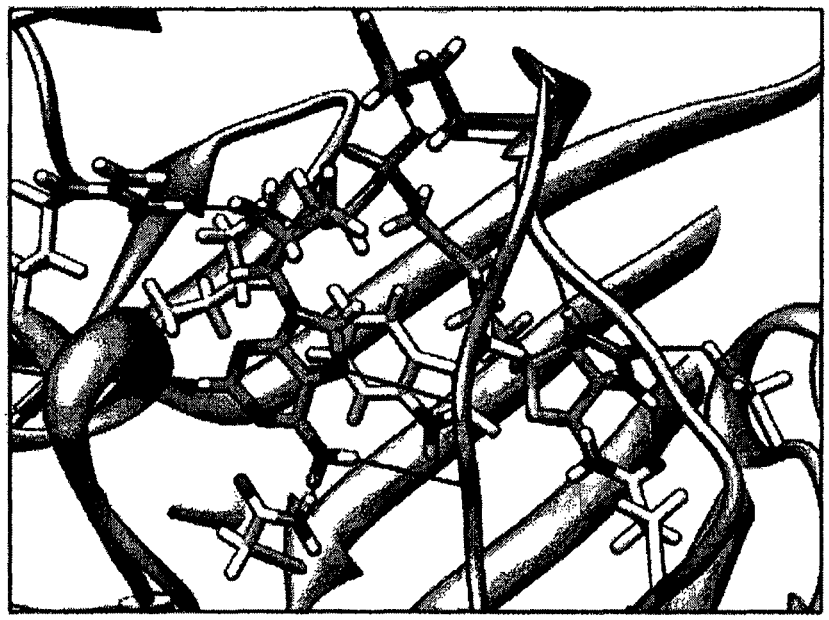

FIG. 4*a* shows the x-ray crystal structure biotinol-5" AMP 2.02 bound in the active site of SaBPL.

Figure 4B:
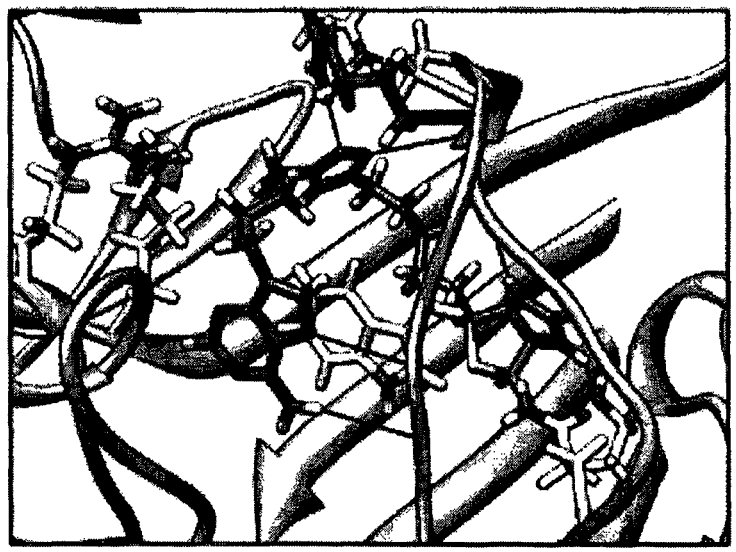

FIG. 4*b* shows the crystal structure of the triazole 4.01 bound in the active site of SaBPL.

Figure 4C:
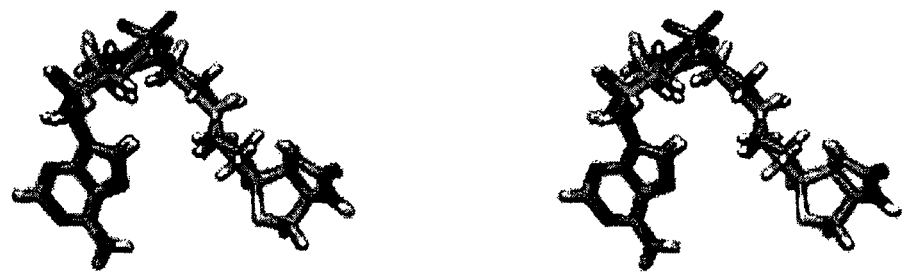

FIG. 4*c* shows the superimposition of the backbone atoms of SaBPL from (4*a*) and (4*b*).

Figure 4D:
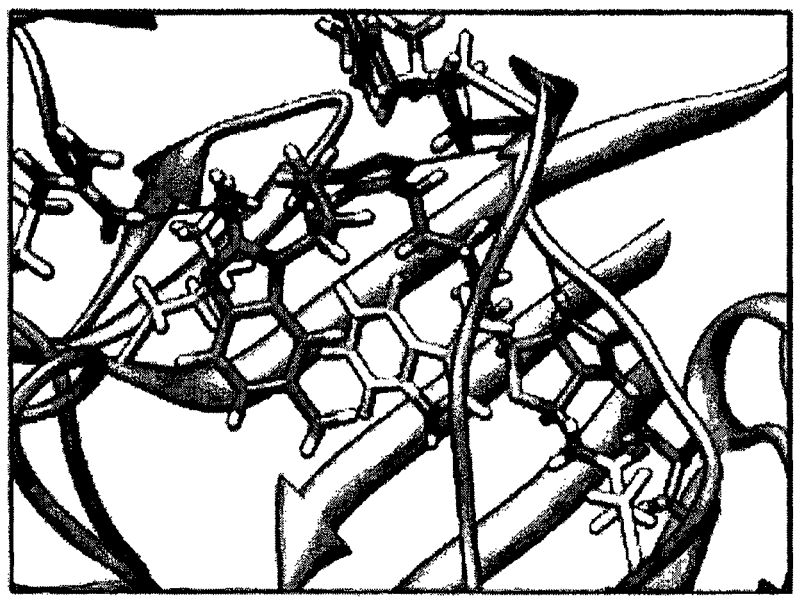

FIG. 4*d* shows the crystal structure of triazole 6.09 bound in the active site of SaBPL.

DETAILED DESCRIPTION OF THE INVENTION

The pharmaceutical compositions of the present invention may be administered by different routes. For example, they may be administered orally in form of pharmaceutically preparations such as tablets, capsules, syrups and suspensions; also, parenterally in form of solutions or emulsions, etc.

They may also be administered topically in form of creams, pomades, balsams, etc. and transdermically for example through the use of patches or bandages. They may also be applied directly in the rectum as suppositories. The preparations may comprise physiologically acceptable carriers, excipients, activators, chelating agents, stabilizers, etc. In case of injections, physiologically acceptable buffers, solubilising agents or isotonics may be added.

The working examples included in the present specification describe in detail suitable processes to obtain several of the compounds according to general formula (I). In the light of these examples, it is within the general knowledge of the expert in the field to obtain the compounds not explicitly exemplified by suitable modifications of the working examples. It is also obvious for the expert in the field that these examples are only illustrative and should not be taken as a limitation of the scope of the invention.

Examples

The synthesis of triazoles 4.01-4.13 utilizes the building blocks alkyne 4.16, 4.17 and 3.12 and azides 4.18-4.21 (shown in Scheme 1A) and involves optimized CuAAC and RuAAC conditions for their coupling (shown in Scheme 1B).

Scheme 1A: Precursors for the synthesis of triazole 4.01-4.15.

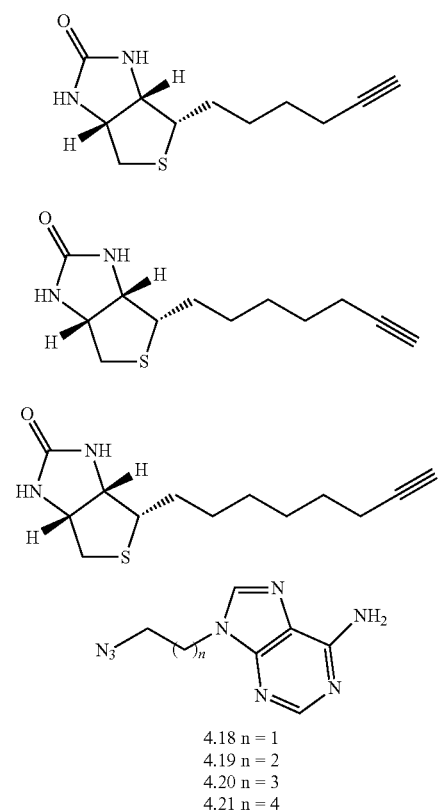

4.18 n = 1
4.19 n = 2
4.20 n = 3
4.21 n = 4

Scheme 1B:

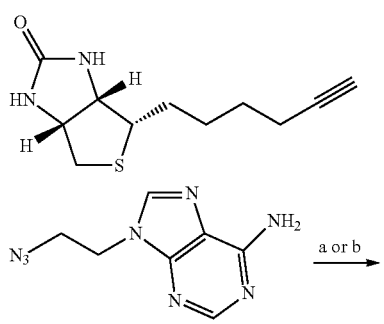

a or b

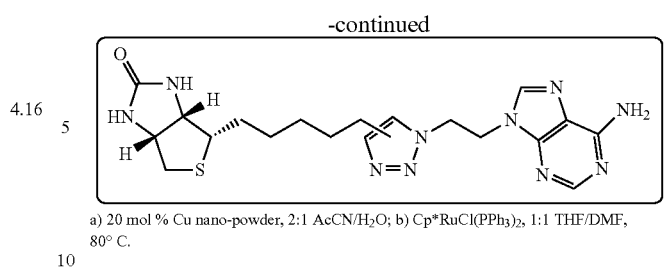

a) 20 mol % Cu nano-powder, 2:1 AcCN/H₂O; b) Cp*RuCl(PPh₃)₂, 1:1 THF/DMF, 80° C.

The synthesis of azides 4.18-4.21 was accomplished from adenine 4.22 as shown in scheme 2. Adenine 4.22 was treated with $K_2CO_3$ and then the appropriate dihalo-alkane 4.23-4.26 in DMF. The resulting halides 4.27-4.31 were then converted to azides 4.19-4.22 on treatment with $NaN_3$ in DMF, with the yields shown in scheme 2.

Scheme 2:

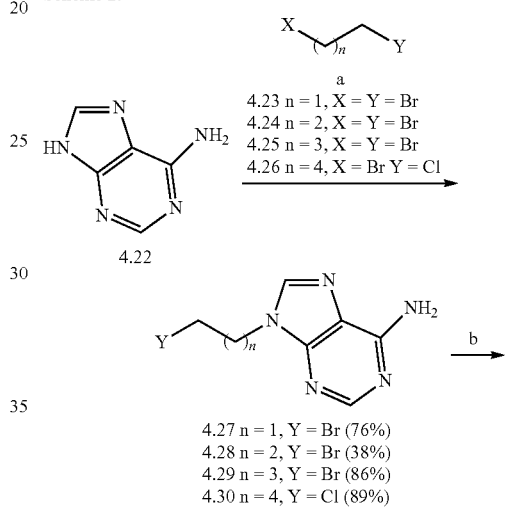

4.27 n = 1, Y = Br (76%)
4.28 n = 2, Y = Br (38%)
4.29 n = 3, Y = Br (86%)
4.30 n = 4, Y = Cl (89%)

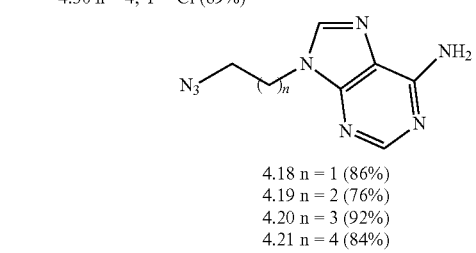

4.18 n = 1 (86%)
4.19 n = 2 (76%)
4.20 n = 3 (92%)
4.21 n = 4 (84%)

a) alkyl dihalide 4.23-4.26, $K_2CO_3$, DMF; b) $NaN_3$, DMF

Access to the norbiotin alkyne 4.16 required the conversion of the amine functionality of 4.34 to the alcohol of 4.35.

Scheme 3:

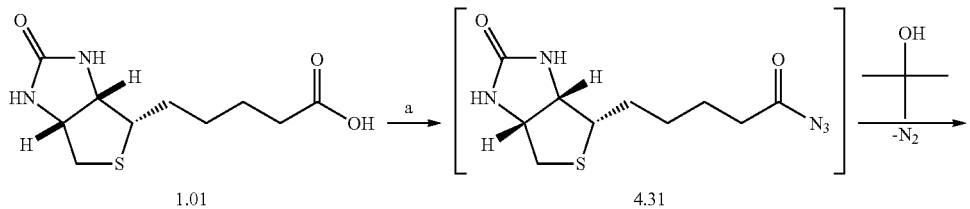

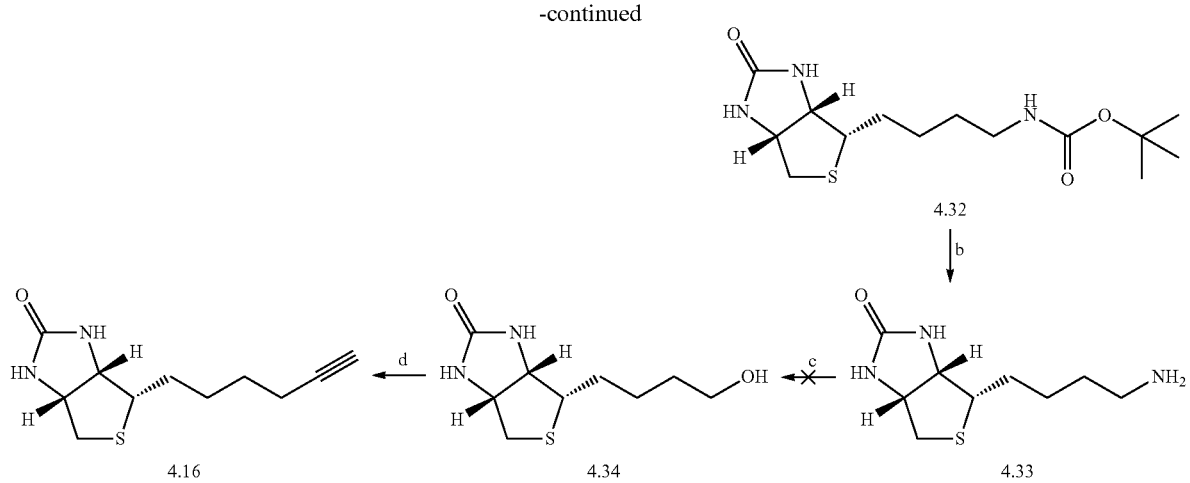

a) DPPA, Et₃N, tert-BuOH; b) 6N HCl, H₂O; c) NaNO₂, AcOH, 1:1 THF/H₂O or Na₂[Fe(CN)₅NO]•2H₂O, NaOH, H₂O; d) i) TsCl, py; ii) LiBr, 2-butanone, iii) Li-acetylide EDA, DMSO.

Biotin 1.01 was treated with diphenylphosphoryl azide (DPPA) and triethylamine in tert-butanol under reflux to give acyl azide 4.31, which underwent a Curitius rearrangement to give the Boc protected biotin amine 4.32 in 51% yield after purification by flash chromatography. Deprotection of the Boc group of 4.32 was achieved on treatment with 6N HCl to give 4.33 in 87% yield without the need for chromatography.

The synthetic route to norbiotin alkyne 4.16 required the radical mediated Barton decarboxylation of biotin to norbiotin bromide 4.38 and subsequent conversion of the bromide to norbiotin alkyne 4.16 as shown in scheme 3.

Biotin 1.01 was converted to the acid chloride 4.35 on treatment with thionyl chloride and DMF in DCM and directly used without further purification in the Barton decarboxylation reaction, as shown in scheme 4. A variety of conditions, such as activation sources (light, heat and AIBN) and solvent systems, were investigated for the Barton decarboxylation of 1.01 to 4.38 (see table 1).

Scheme 4:

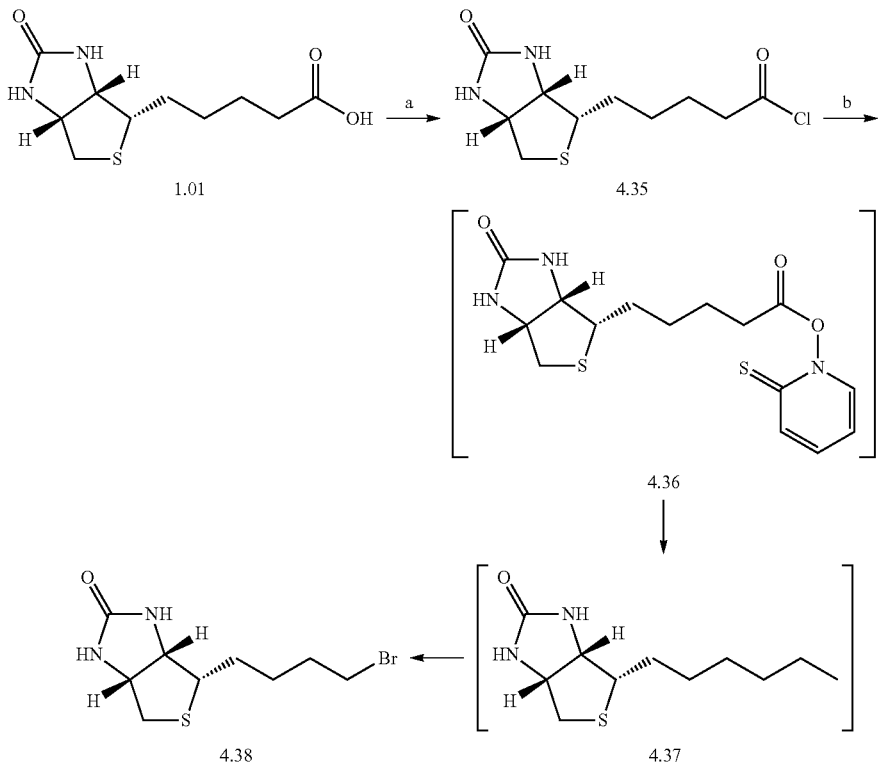

a) SOCl₂, DMF, DCM; b) see table 1 for conditions

TABLE 1

Conditions investigated for the decarboxylation of biotin 4.35 as shown in scheme 4.

| Entry | Solvent | Activation source | Additives | Yield[a] |
|---|---|---|---|---|
| 1 | BrCCl$_3$ | Heat (80° C.)[a] | — | 1% |
| 2 | BrCCl$_3$ | RT/Light[b] | — | Trace |
| 3 | BrCCl$_3$ | Heat (80° C.)/light[b] | — | 1% |
| 4 | BrCCl$_3$ | Heat (80° C.) | AIBN | 3% |
| 5 | BrCCl$_3$ | Heat (80° C.) | 4-DMAP | 1% |
| 6 | 1:1 THF:BrCCl$_3$ | Heat (80° C.) | — | 0% |
| 7 | 1:1 DMF:BrCCl$_3$ | Heat (80° C.) | — | 7% |
| 8 | 2:1 DMF:BrCCl$_3$ | Heat (80° C.) | — | 15% |
| 9 | 8:1 DMF:BrCCl$_3$ | Heat (80° C.) | — | 21% |

[a]Isolated yields after flash chromatography.

As described in Table 1 the Barton decarboxylation of 1.01 was undertaken with solvent mixtures containing 1:1 THF/BrCCl$_3$ (0%, entry 6), 1:1 DMF/BrCCl$_3$ (7%, entry 7), 2:1 DMF/BrCCl$_3$ (15%, entry 8) and 8:1 DMF/BrCCl$_3$ (21%, entry 9). Here it was found a 8:1 DMF/BrCCl$_3$ gave the greatest increase in yields of biotin 4.38 (entry 11).

With sufficient norbiotin bromide 4.38 in hand, the synthesis of norbiotin alkyne 4.16 was undertaken (see scheme 5). Norbiotin bromide 4.38 was treated with lithium acetylide EDA complex in DMSO to give norbiotin alkyne 4.16 in 41% yield after flash chromatography. Norbiotin alkyne 4.16 was utilised for the synthesis of triazole 4.09 and 4.11 described below.

Scheme 5:

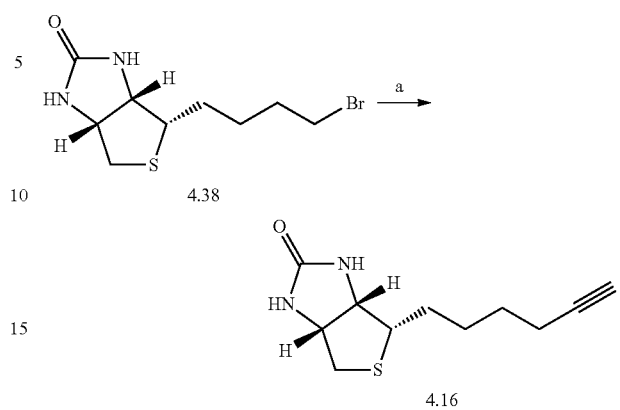

a) Li-acetylide EDA complex, DMSO;

Homobiotin Alkyne 4.17

The synthesis of homobiotin alkyne 4.17 is shown in scheme 6. This synthetic approach involved access to the reported synthesis of homobiotin 4.40, followed by functional group transformation to give homobiotin alkyne 4.17.

Scheme 6:

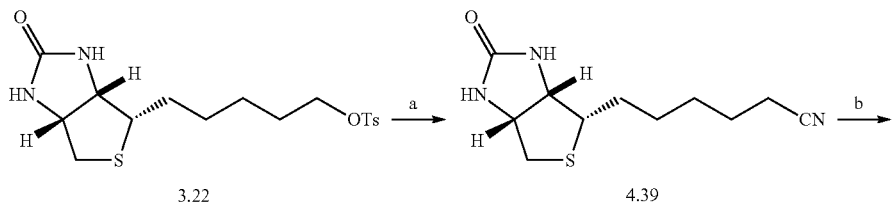

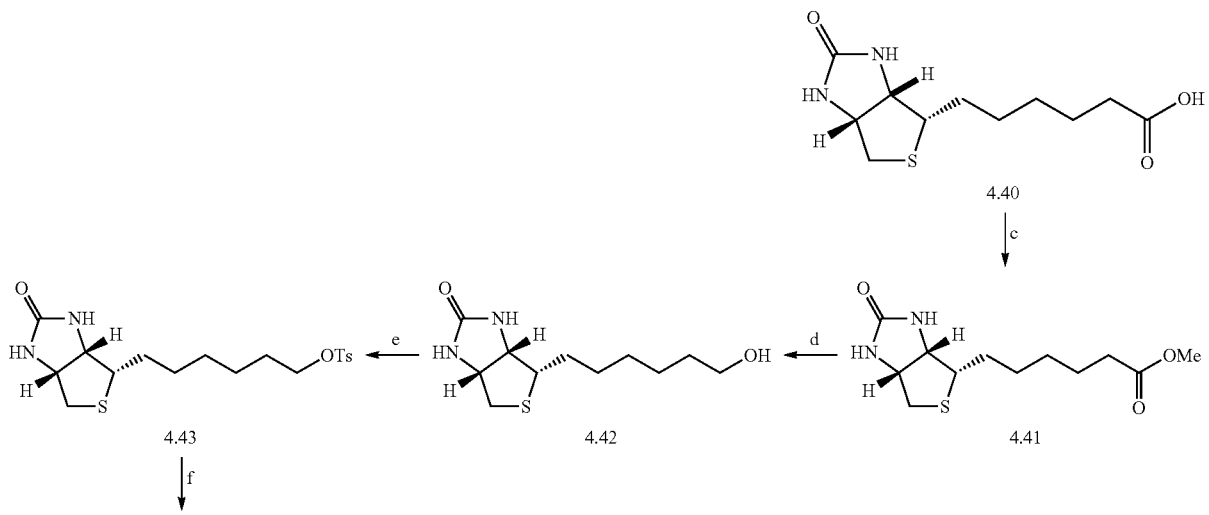

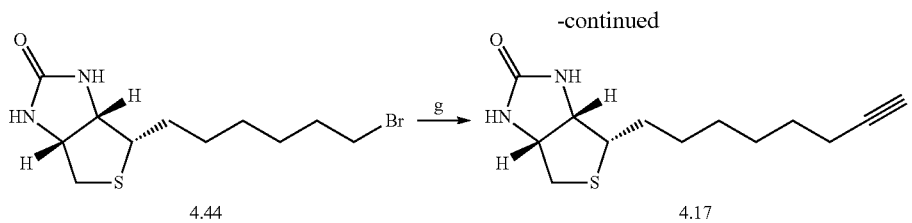

a) KCN, DMF; 6N b) NaOH, H$_2$O, reflux; c) SOCl$_2$, MeOH; d) LiAlH$_4$, THF; e) TsCl, py; f) LiBr, MEK; g) Li-acetylide EDA, DMSO.

Biotin tosylate 3.22 was treated with sodium cyanide in DMF at ambient temperature to give nitrile 4.39 in 72% yield. Hydrolysis of nitrile 4.39 with 4 N sodium hydroxide under reflux, followed by acidification with 6 N HCl gave homobiotin 4.40 in 96% yield after vacuum filtration and without further purification. Acid esterification with thionyl chloride gave methyl ester 4.41 in quantitative yields, which was reduced with LiAlH$_4$ to give homobiotinol 4.42 in 91% yield. Conversion of homobiotinol 4.42 to the tosylate 4.43 was achieved on reaction with tosyl chloride in pyridine. The crude tosylate 4.43 was treated with lithium bromide in 2-butanone under reflux to give homobiotin bromide 4.44 in 51% yield over two steps from homobiotinol 4.42 and after flash chromatography. Finally, addition of lithium acetylide EDA complex to homobiotin bromide 4.44 in DMSO at 15° C. gave homobiotin acetylene 4.17 in 36% yield.

Synthesis of Triazoles 4.01-4.13 Via CuAAC (Copper Catalyzed Azide-Alkyne Cycloadditions) and RuAAC (Ruthenium Catalyzed Azide-Alkyne Cycloadditions)

The synthesis of triazoles 4.01-4.04, 4.12 and 4.13 is shown in scheme 7 with yields reported therein. The appropriate alkyne and azide were dissolved in 2:1 acetonitrile and water mixture treated with 20 mol % copper nano powder, sonicated for 15 min and stirred at 35° C. for 4 h. Due to the low solubility of azide 4.19, the CuAAC formation of 4.02 was accomplished in solvent mixture of acetonitrile:water: DMSO (5:4:1). The 1,4-triazole regioisomer configuration of 4.01-4.04, 4.12 and 4.13 were confirmed by $^1$H NMR ROESY and COSY experiments.

Synthesis of Triazole 4.01-4.13 Via CuAAC and RuAAC

The synthesis of triazoles 4.01-4.04, 4.12 and 4.13 is shown in scheme 7 with yields reported therein. The appropriate alkyne and azide were dissolved in 2:1 acetonitrile and water mixture treated with 20 mol % copper nano powder, sonicated for 15 min and stirred at 35° C. for 4 h. Due to the low solubility of azide 4.19, the CuAAC formation of 4.02 was accomplished in solvent mixture of acetonitrile:water: DMSO (5:4:1). The 1,4-triazole regioisomer configuration of 4.01-4.04, 4.12 and 4.13 were confirmed by $^1$H NMR ROESY and COSY experiments.

Scheme 7:

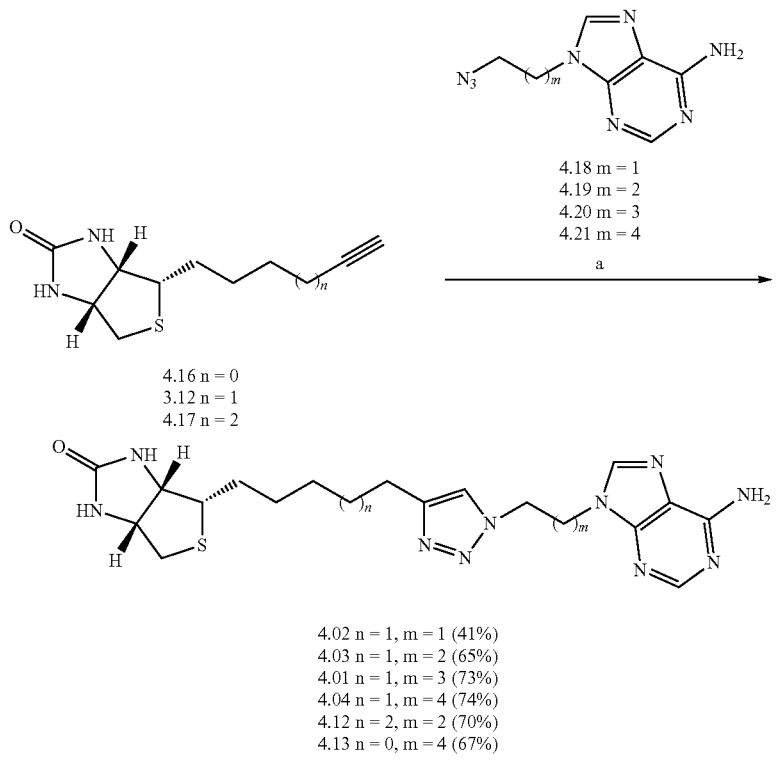

a) Cu nano-powder, 2:1 acetonitrile/water, sonication, 40° C.

The synthesis of triazoles 4.09 and 4.10, shown in scheme 8, retained the pentose ring as both triazoles 4.09 and 4.10 were initially developed as analogues of triazole 3.25. Thus alkynes 4.16 and 4.17 were treated separately with azide 3.16 in 2:1 acetonitrile and water mixture containing 20 mol % copper nano powder. Triazoles 4.09 and 4.10 were purified with flash chromatography with isolated yields of 68% and 61% respectively.

Scheme 8:

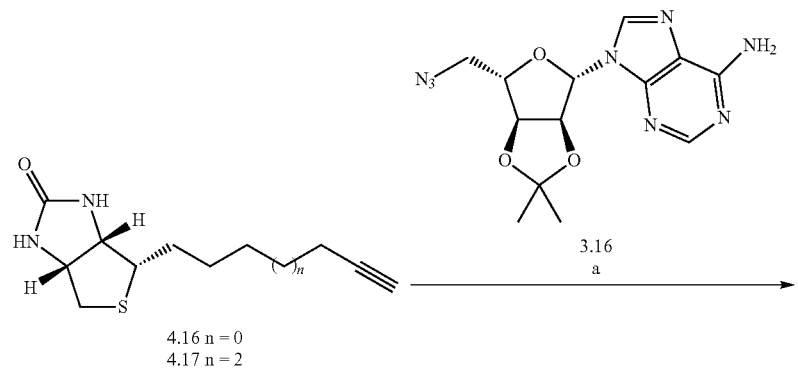

4.16 n = 0
4.17 n = 2

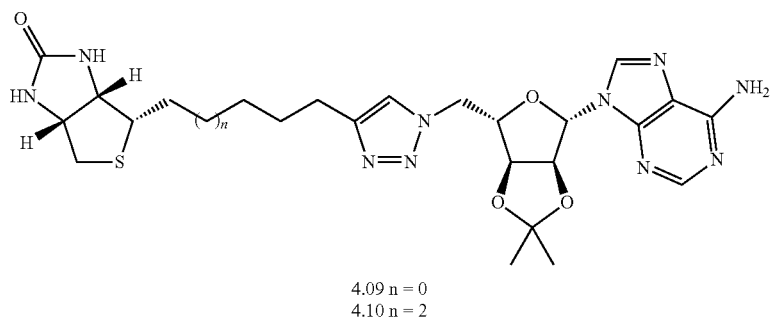

4.09 n = 0
4.10 n = 2 a) Cu nano-powder, 2:1 acetonitrile/water, sonication, 35° C.

The synthesis of triazoles 4.05-4.08 is shown in scheme 9. Azides 4.18-4.21 were treated with alkyne 3.12 and Cp*Ru (PPh$_3$)$_2$Cl in 1:1 DMF and THF solvent mixture at 80° C. The resulting triazoles 4.05-4.08 were isolated and purified by flash chromatography in yields reported in scheme 9. The 1,5-triazole configurations of 4.05-4.08 were confirmed by $^1$H NMR ROESY and COSY experiments.

Scheme 9:

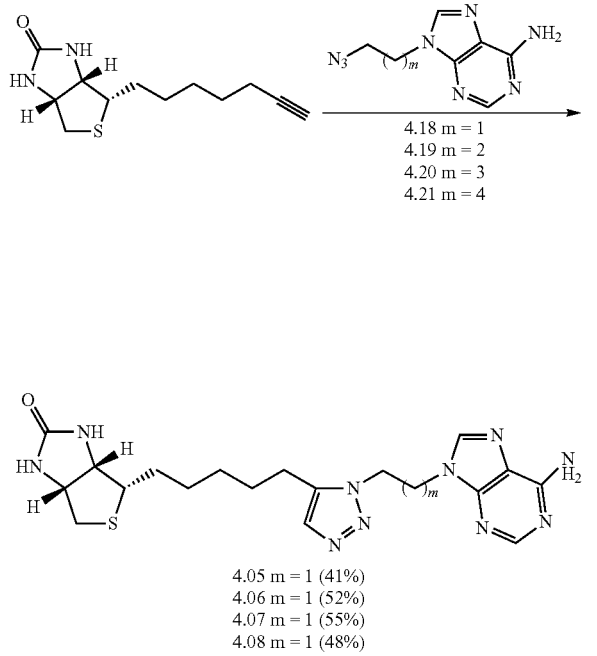

4.05 m = 1 (41%)
4.06 m = 1 (52%)
4.07 m = 1 (55%)
4.08 m = 1 (48%)

a) Cp*Ru(PPh$_3$)$_2$Cl, 2:1 THF\DMF, 80° C.

Determination of 1,4 and 1,5 Regioisomer of Triazoles 4.01-4.13

1D $^1$H NMR and 2D COSY of triazoles 4.01-4.13 confirmed that a single regioisomer was present. The chemical shifts of the triazole H5 resonances are tabulated in table 4. 2D ROESY $^1$H NMR experiments indicated the 1,4- and 1,5-triazoles 4.01-4.12 possess distinguishable through space interactions with adjacent methylene protons (H$_A$ and H$_C$) and 5 position upon the triazole ring (H$_B$) (see table 4). The 1,4-triazoles (4.01-4.04, 4.09-4.12) were found to provide the diagnostic through space interactions between the triazole proton H$_B$ and both adjacent methylene protons H$_A$ and H$_C$ (see table 4). Conversely, the 1,5-triazoles (4.05-4.08) only possessed through space interactions between methylene H$_B$ and triazole H$_A$.

However, other cyclic structures present as group R$_1$ in formula (I) are also useful, structures such as, by way of example only, when R$_1$ is selected from the group consisting of:

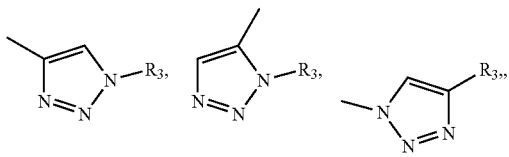

pyrazole,

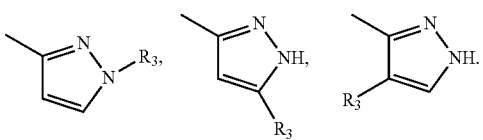

These inhibitors are attractive compared to the non-selective BPL inhibitor biotinol-5'-AMP

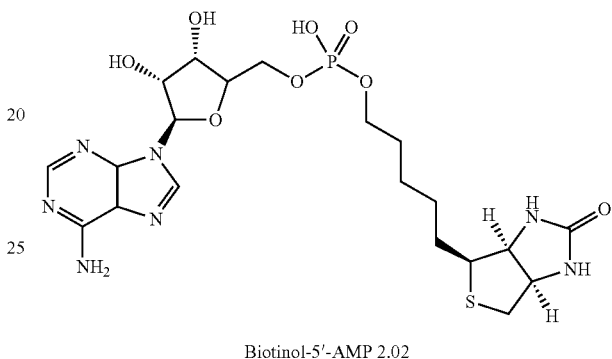

Biotinol-5'-AMP 2.02

Synthesis of Azide Building Blocks 6.16, 6.17, 6.22-6.25 and 6.31-6.33

Figure 2:
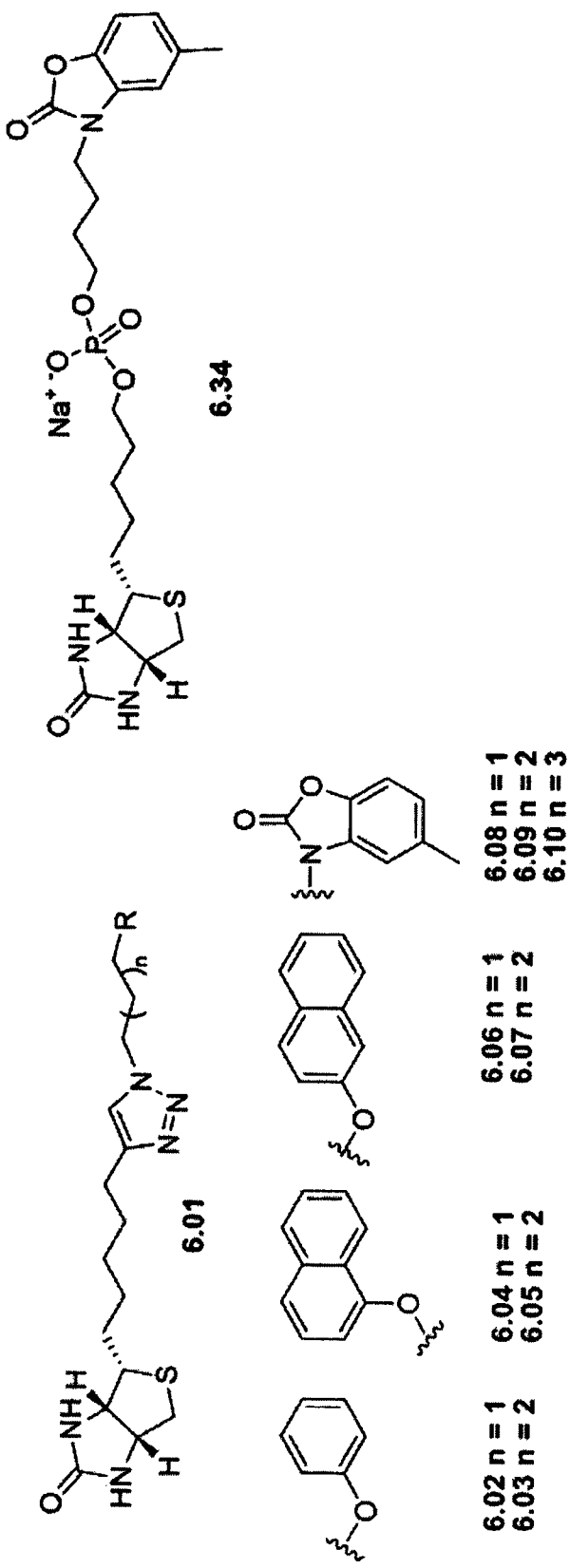
FIG. 2 shows the triazole analogues 6.02-6.10 and phosphodiester 6.34 of the present invention.

A retrosynthetic analysis of these triazole structures (6.02-6.10) FIG. 2 reveals the azide building blocks 6.16, 6.17, 6.22-6.25 and 6.31-6.33 which would be coupled to alkyne 3.12. The azides were prepared as shown in schemes 10 and 11.

Phenol was treated with potassium carbonate and the resulting phenoxide separately alkylated with alkyl dihalide 6.12 and 6.13 to give 6.14 and 6.15 respectively, see Scheme 10. The halides 6.14 and 6.15 were then reacted with sodium azide in DMF to give the azide 6.15 and 6.16. The synthesis of 1-naphthyl 6.22 and 6.23 and 2-naphthyl 6.24 and 6.25 were similarly prepared from 1-naphthol and 2-naphthol respectively and followed the same conditions as phenyl 6.15 and 6.16. Formation of the azides was confirmed by FT-IR spectroscopy with absorptions between 2093-2098 cm$^{-1}$ Scheme 10:

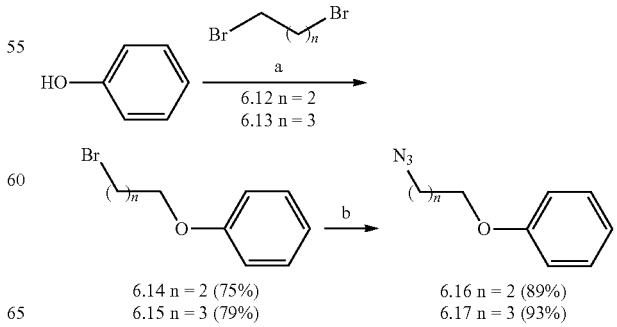

6.14 n = 2 (75%)
6.15 n = 3 (79%)

6.16 n = 2 (89%)
6.17 n = 3 (93%)

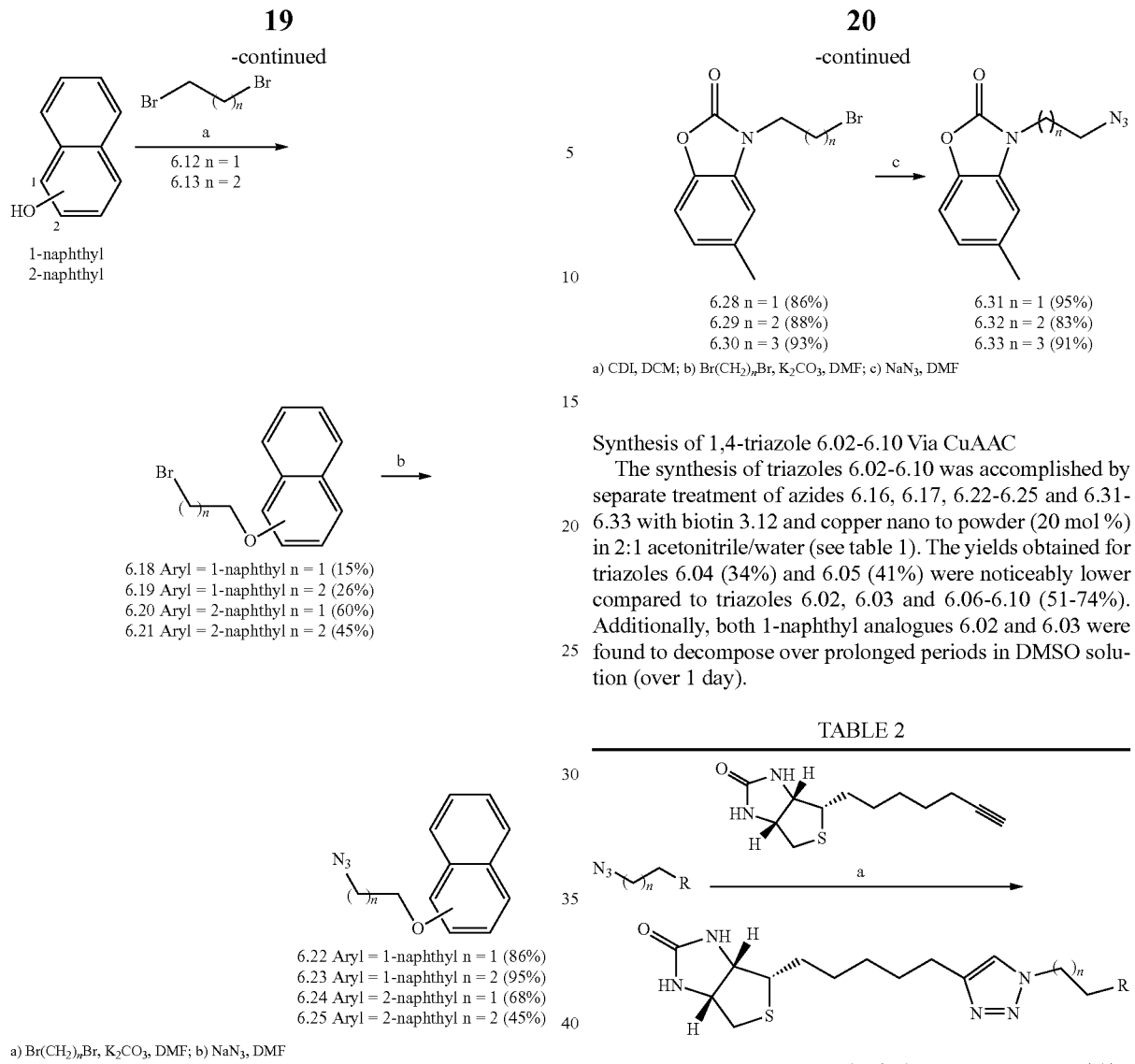

a) CDI, DCM; b) Br(CH$_2$)$_n$Br, K$_2$CO$_3$, DMF; c) NaN$_3$, DMF

Synthesis of 1,4-triazole 6.02-6.10 Via CuAAC

The synthesis of triazoles 6.02-6.10 was accomplished by separate treatment of azides 6.16, 6.17, 6.22-6.25 and 6.31-6.33 with biotin 3.12 and copper nano powder (20 mol %) in 2:1 acetonitrile/water (see table 1). The yields obtained for triazoles 6.04 (34%) and 6.05 (41%) were noticeably lower compared to triazoles 6.02, 6.03 and 6.06-6.10 (51-74%). Additionally, both 1-naphthyl analogues 6.02 and 6.03 were found to decompose over prolonged periods in DMSO solution (over 1 day).

2-Benzoxazolone 6.27 was obtained by cyclising 2-amino-cresol with CDI as shown in Scheme 11. This material was treated with potassium carbonate followed by separate reactions with alkyl dihalide 6.26, 6.12 and 6.13 in DMF, to give halide 6.28-6.30 respectively. The halides 6.28-6.30 were converted to the azides 6.31-6.33 on reaction with sodium azide in DMF as shown in scheme 11.

Scheme 11:

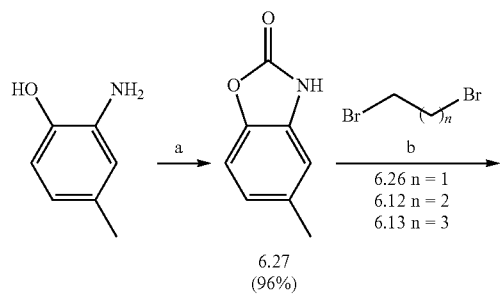

TABLE 2-continued

[Reaction scheme: biotin alkyne + N₃-(CH₂)ₙ-R → biotin-triazole-R, condition a]

| Reactant | R (product) | n = | Yield[a] |
|---|---|---|---|
| 6.23 | 1-naphthyloxy (6.05) | 2 | 41% |
| 6.24 | 2-naphthyloxy (6.06) | 2 | 51% |
| 6.25 | 2-naphthyloxy (6.07) | 1 | 74% |
| 6.31 | 5-methylbenzoxazol-2(3H)-one-N-yl (6.08) | 2 | 65% |

TABLE 2-continued

[Reaction scheme: biotin alkyne + N₃-(CH₂)ₙ-R → biotin-triazole-R, condition a]

| Reactant | R (product) | n = | Yield[a] |
|---|---|---|---|
| 6.32 | 5-methylbenzoxazol-2(3H)-one-N-yl (6.09) | 3 | 64% |
| 6.33 | 5-methylbenzoxazol-2(3H)-one-N-yl (6.10) | 1 | 69% |

[a]Isolated yields after flash chromatography

Figure 1:
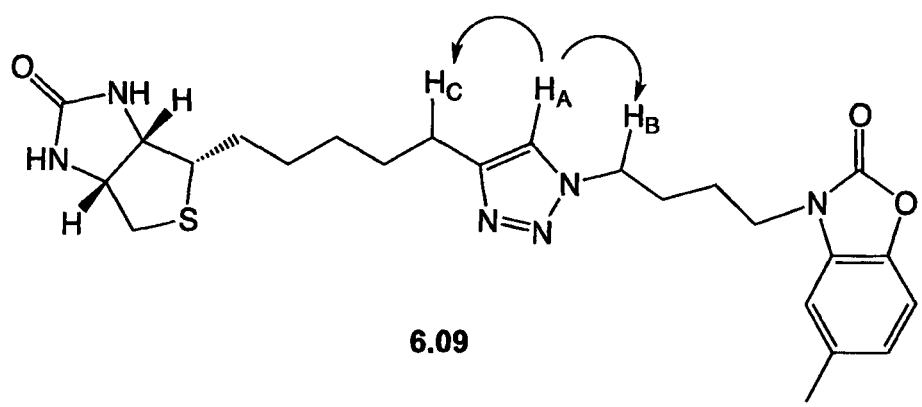
FIG. 1 is a depiction of through space interactions with arrows indicating the interactions observed in ROESY 2D $^1$H NMR experiment.

2D ROESY NMR of structures 6.03, 6.07 and 6.09 indicated through space coupling between protons $H_A$ and $H_B$ with $H_A$ and $H_C$, suggesting the 1,4-di substitution pattern was obtained over 1,5-disubstitution pattern, see FIG. 1. An X-ray crystal structure of triazole 6.09 bound to SaBPL confirmed the binding mechanism of the 1,4-disubstitution pattern.

Design and Synthesis of Phosphodiester 6.34

The biotin triazole inhibitors were found to be potent and selective against SaBPL with triazole 4.01 ($K_i$=0.66±0.15 μM) and triazole 6.09 ($K_i$=0.09±0.02 μM) as the leading examples. However, triazoles 4.01 and 6.09 were found to be between 22 and 3 fold less potent against SaBPL, respectively, compared to the phosphodiester containing inhibitor, biotinol-5'-AMP 2.02 ($K_i$ 0.03±0.001 μM).

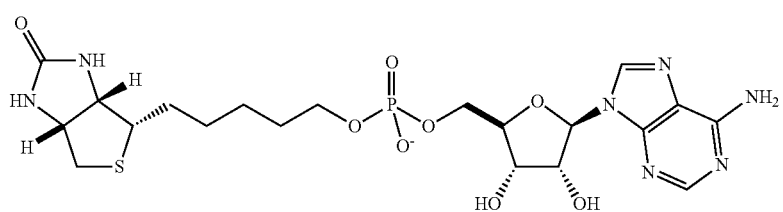

2.02

-continued
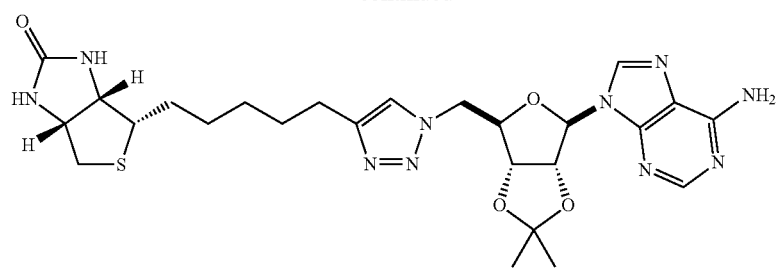
3.25
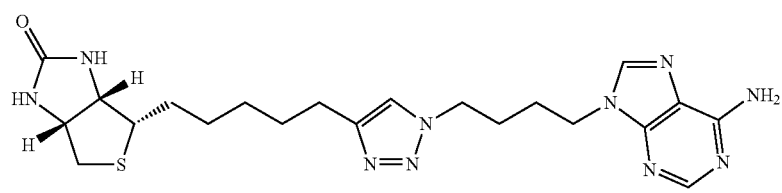
4.01
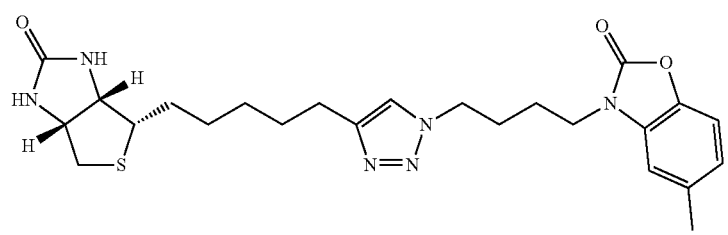
6.10
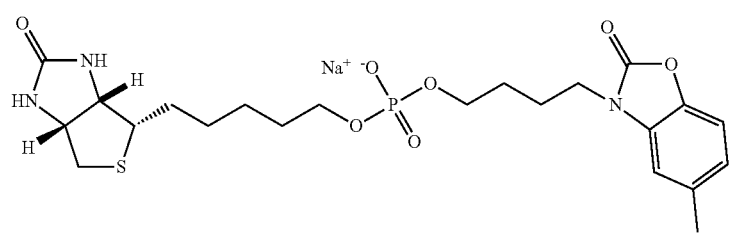
6.34

Synthesis of Phosphodiester 6.34

The synthetic pathway to benzoxazolone 6.34 is shown in scheme 13.

halide alcohol as shown in scheme 13. Phosphitylation of 6.35 with N,N-diisopropyl-methoxyphosphonamidic chloride gave the phosphite 6.37 in 67% as a crude yield. The

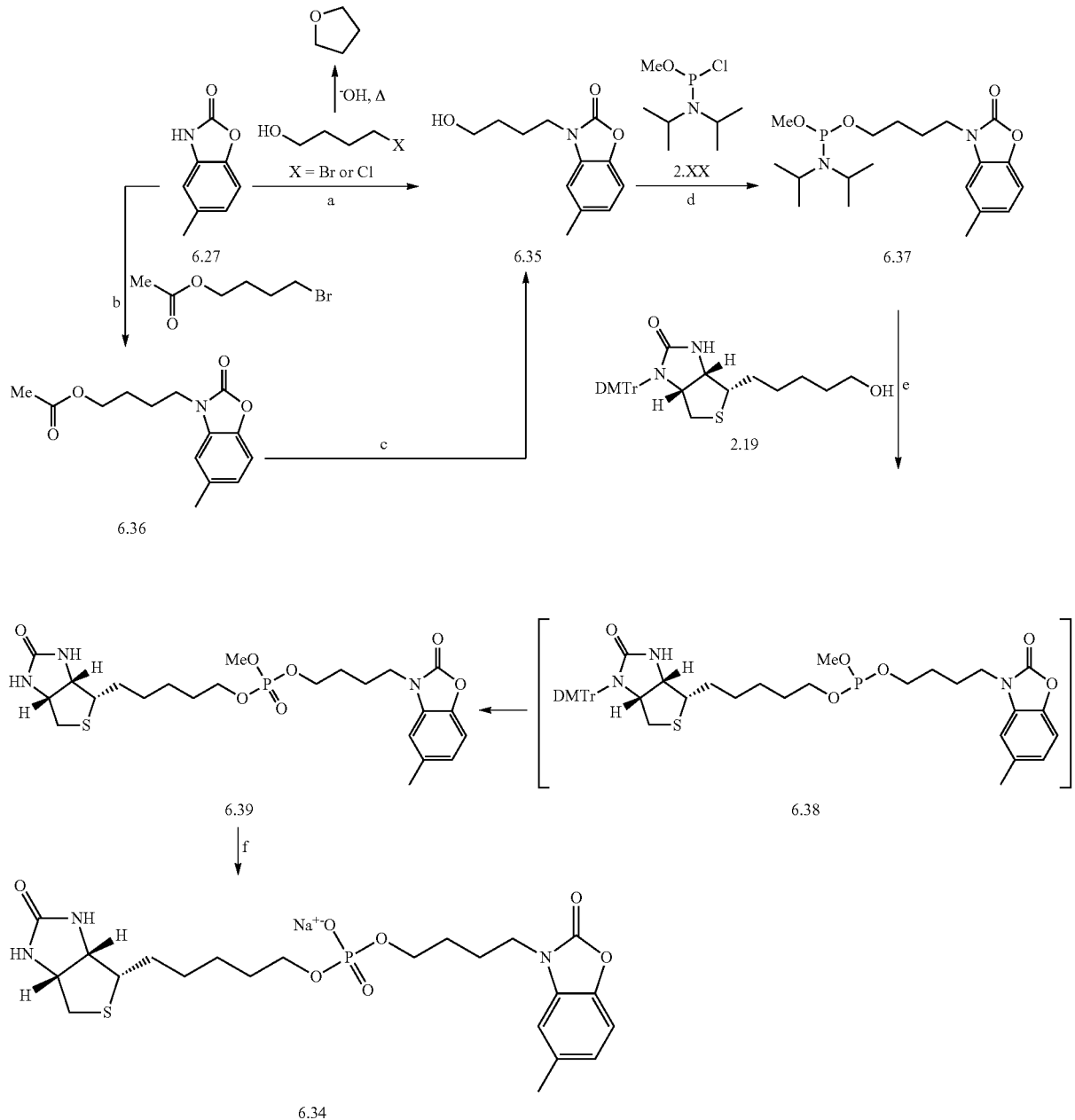

Scheme 13:

a) NaOH, H₂O, Δ; b) K₂CO₃, TBAI, DMF; c) LiOH, 1:1 THF/H₂O d) Et₃N, DCM; e) i) 5-ethylthiotetrazole, AcCN; ii) TBHP; iii) 5a% TFA, DCM; f) NaI, acetone, Δ

The synthesis of phosphodiester 6.34 required access to the phosphite precursor 6.37. This was achieved through the alkylation of benzoxazolone with 4-bromo-butyoxylacetate to give 6.36 in 78% yield, followed by the deprotection of the acetate group to give 6.35 in 78% yield. Following literature procedures, the initial synthesis of alcohol 6.35 was achieved with treatment of 6.27 with both 4-bromobutanol and 4-chlorobutanol separately, but gave low yields of 5% and 11% respectively. The cause for the low yields was suggested to be the result of a base mediated intramolecular cyclization of the crude phosphoramidite 6.37 was subsequently treated with 5-ethylthio-tetrazole and DMTr-biotinol 2.19 in acetonitrile to give 6.38, the phosphite of which was oxidised with tert-butoxyl hydrogen peroxide and acidification with 5% TFA gave phosphotriester 6.39 in 39% yield from 6.35. Finally, the demethylation of 6.39 was achieved on reaction with NaI in acetone under reflux to give 6.34 in 67% yield after purification by reverse phase HPLC

TABLE 4 summary of $^1$H NMR ROESY experiments on triazole 4.01-4.12.

1,4-triazole 1,5-triazole

| Triazole | m | n | Method[a] | $H_A$ (ppm) | $H_B$ (ppm) | $H_C$ (ppm) | $^1$H NMR ROESY interaction[e] | Substitution pattern |
|---|---|---|---|---|---|---|---|---|
| 4.02[b] | 1 | 2 | A | 2.58 | 7.74 | 4.86 | $H_a$ and $H_c$ | 1,4 |
| 4.05[b] | 1 | 2 | B | 2.35 | 7.48 | 4.78 | $H_a$ | 1,5 |
| 4.03[c] | 1 | 3 | A | 2.66 | 7.34 | 4.31 | $H_a$ and $H_c$ | 1,4 |
| 4.06[c] | 1 | 3 | B | 2.38 | 7.50 | 4.26 | $H_a$ | 1,5 |
| 4.01[b] | 1 | 4 | A | 2.61 | 7.83 | 4.37 | $H_a$ and $H_c$ | 1,4 |
| 4.07[c] | 1 | 4 | B | 2.55 | 7.43 | 4.35 | $H_a$ | 1,5 |
| 4.04[c] | 1 | 5 | A | 2.68 | 7.28 | 4.31 | $H_a$ and $H_c$ | 1,4 |
| 4.08[c] | 1 | 5 | B | 2.50 | 7.36 | 4.15 | $H_a$ | 1,5 |
| 4.09[c] | 0 | Pentose[a] | A | 2.68 | 7.12 | 5.58 | $H_a$ and $H_c$ | 1,4 |
| 4.10[d] | 2 | Pentose[a] | A | 2.60 | 7.13 | 4.70 | $H_a$ and $H_c$ | 1,4 |
| 4.11[c] | 0 | 3 | A | 2.78 | 7.48 | 4.41 | $H_a$ and $H_c$ | 1,4 |
| 4.12[c] | 2 | 5 | A | 2.69 | 7.25 | 4.31 | $H_a$ and $H_c$ | 1,4 |

[a]Method A: Cu nano-powder, 2:1 acetonitrile/water, sonication, 35° C., Method B: Cp*Ru(PPh$_3$)$_2$Cl, 2:1 THF\DMF, 80° C.
[b]$^1$H NMR was obtained with DMSO-d$_6$.
[c]$^1$H NMR was obtained with CDCl$_3$ and 5% CD$_3$OD
[d]$^1$H NMR was obtained with CDCl$_3$.
[e]observed through space interactions with respect to $H_B$.

Biological Data
Enzyme Inhibition Assays

Quantitation of BPL catalysed $^3$H-biotin incorporation into the biotin domain substrate was performed as previously described by Polyak et al, J. Biol. Chem (1999) 274(46) 32847-54. Briefly, the reaction mixture contained: 50 mM Tris HCl pH 8.0, 3 mM ATP, 4.5 μM biotin, 0.5 μM $^3$H-biotin, 5.5 mM MgCl$_2$, 100 mM KCl, 0.1 mg/mL BSA and 10 μM biotin domain of S. aureus pyruvate carboxylase. The reaction was initiated by the addition of BPL to a final concentration of 4 nM. After 20 minutes at 37° C., 4 μL aliquots of the reaction were spotted onto Whatman paper pre-treated with biotin and trichloroacetic acid. The filters were washed twice with 10% v/v ice-cold trichloroacetic acid and once with ethanol before air-drying. Quantitation of protein-bound radiolabelled biotin was performed by liquid scintillation. One unit of enzyme activity was defined by the amount of BPL required to incorporate 1 nmol of biotin per minute. The IC$_{50}$ value of each compound was determined from a dose-response curve by varying the concentration of the inhibitor under the same enzyme concentration. The data was analysed with GraphPad Prism using a non-linear fit of log$_{10}$ (inhibitor) vs. normalized response. The K$_i$, the absolute inhibition constant for a compound, was determined using Eq 1:

$$K_i = \frac{IC_{50}}{1 + \frac{[S]}{K_m}} \qquad \text{Eq1.}$$

where K$_m$ is the affinity of the substrate for the enzyme ([biotin]=1 μM) and [S] is the substrate concentration ([biotin]=5 μM).

The mode of inhibition was investigated by varying the concentrations of inhibitor alongside varying the concentrations of $^3$H-biotin. The data was plotted as double reciprocal plots and assessed using Lineweaver-Burk analysis.

Triazoles 6.02-6.10 were assayed for inhibitory activity against the biotin protein ligases from S. aureus (SaBPL), Escherichia coli (EcBPL) and Homo sapiens (HsBPL) (Table 3). The inhibitory activity of the compounds was determined by measuring BPL activity with varying concentrations of inhibitors. From the dose-response curves IC$_{50}$ values were determined and Ki values calculated. Results are shown in Table 3.

TABLE 3

Selected triazole analogues and their inhibition assay results against SaBPL, EcBPL and HsBPL.

| Compound | SaBPL $K_i$ (μM) | SaBPL $IC_{50}$ (μM) | EcBPL $K_i$ (μM) | HsBPL $K_i$ (μM) |
|---|---|---|---|---|
| 3.25 | 1.83 ± 0.33 | 11.6 ± 2.2 | >30* | >30* |
| 6.09 | 0.09 ± 0.02 | 0.53 ± 0.01 | >30 | >30 |
| 6.07 | 1.17 ± 0.17 | 7.0 ± 1.0 | >30 | >30 |
| 4.01 | 0.66 + 0.05 | 4.0 ± 0.9 | >30 | >30 |
| 6.34 | >10 | >50 | ND | ND |
| 2.02 | 0.03 ± 0.001 | 0.203 ± 0.02 | 0.42 ± 0.017 | 0.225 ± 0.01 |

*Solubility of the compound was limiting and prevented further quanititation.

The triazole compounds in the SAR series demonstrated excellent selectivity for SaBPL over the isozymes from *E. coli* and human. Against SaBPL, the biotin triazoles inhibited SaBPL with potency of 1 μM or better. Against human and *E. coli* BPLs, biotin triazoles were included in the assay at the highest concentration at which they remained soluble (200 μM) with no inhibitory activity measurable.

Compound 3.25 is a structural homologue of the BPL reaction intermediate biotinyl-5-AMP and inhibitor biotinol-5-AMP 2.02, where the phosphate linkages have been substituted with a 1,4 triazole. Biotin triazole 3.25 was 60-fold less potent than 2.02, but displayed much higher selectivity than the pan inhibitor (2.02=7.5-fold Hs vs SaBPL; 3.25=>>16-fold Hs vs SaBPL). Removal of the ribose moiety from 3.25 improved potency by 3-fold in the lead structure 4.01.

2-Naphthyl 6.07 was found to be potent and selective against SaBPL with Ki 1.17±0.17 μM. Although 2-Naphthyl 6.07 is less effective compared to the parent lead structure of adenine 4.01 (7 fold decrease), the retained selectivity towards SaBPL highlights the 1,2,3-triazole ring as the component required for selectivity.

Benzoxazolone 6.09 was the most potent and selective example towards SaBPL with $K_i=0.09\pm0.02$ μM. This inhibitor is made more remarkable by its 7 fold increase in potency compared to the lead adenine structure 4.01 and only a 3 fold decrease in potency compared to the non-selective biotinol-5'-AMP 2.02. Importantly, the biotin triazole showed selectivity of >1000-fold towards SaBPL over both human and E. coli BPL (FIG. 3a).

Antimicrobial Assays

The biotin-triazoles were assessed for their antimicrobial activity using a microbroth dilution assay as recommended by the CLSI (Clinical and Laboratory Standards Institute, Document M07-A8, 2009, Wayne, Pa.) with cation-adjusted Mueller-Hinton broth (Trek Diagnostics Systems, U.K.). Compounds were dissolved using DMSO. Serial two-fold dilutions of each compound were made using DMSO as the diluent. Trays were inoculated with $5\times10^4$ CFU of each strain in a volume of 100 μL (final concentration of DMSO was 5% (v/v)), and incubated at 35° C. for 16-20 hours when the optical density of the growth cultures was measured by spectroscopy at wavelength 620 nm.

A library of Gram negative and Gram positive microbes was employed. The antimicrobial assay results revealed benzoxazolone 6.09 prevented cell growth of S. aureus ATCC 49775 by 80% at 8 μg/ml (FIG. 3b). However, no inhibition of growth was observed for other Gram negative microbes such as Enterococcus faecalis or Enterococcus faecium.

Cell Culture Toxicity

HepG2 cells were suspended in Dulbecco-modified Eagle's medium containing 10% fetal bovine serum, and then seeded in 96-well tissue culture plates at either 5 000, 10 000 or 20 000 cells per well. After 24 hours, cells were treated with varying concentrations of compound, such that the DMSO concentration was consistent at 4% (v/v) in all wells. After treatment for 24 or 48 hours, WST-1 cell proliferation reagent (Roche) was added to each well and incubated for 0.5 hours at 37° C. The WST-1 assay quantitatively monitors the metabolic activity of cells by measuring the hydrolysis of the WST-1 reagent, the products of which are detectable at absorbance 450 nm.

The biotin triazoles also exhibited no toxicity when using a human HepG2 cell culture model (FIG. 3c). This concurs with the limited activity of the biotin triazoles against HsBPL ($IC_{50}$>200 μM).

In FIG. 3a, differential inhibition. BPL activity was measured in vitro with varying concentrations of biotin triazole 6.09. The assays were performed using recombinant BPL from S. aureus (♦), E. coli (○) and H. sapiens (X).

FIG. 3b shows anti-staphylococcus activity. Inhibition of the growth of S. aureus ATCC 49775 was measured using a microbroth dilution assay with varying concentrations of BPL inhibitors. The graph shows the effect of including the following in the growth media: biotinol-5-AMP 2.02 (○), biotin triazoles 4.01 (◇) and 6.09 (●), and no inhibitor (■). The antibiotic erythromycin was also included (X).

In FIG. 3c, the cytotoxicity of the biotin triazole series was assessed on HepG2 cells using a cell proliferation assay. Cells were seeded at either 20000, 1000 or 5000 cells per well and treated for 48 hours with media containing 64 μg/ml of compound and 2% DMSO. The treatments in this series were (from left to right) DMSO vehicle (small hatch), BPL043 (large hatch), 3.25 (horizontal stripe), 4.01 (verticle stripe), 6.09 (upward diagonal stripe) and 6.07 (downward diagonal stripe). X-ray crystallography The mechanism of biotin triazoles binding to SaBPL was verified by X-ray crystallography. Apo-SaBPL was buffer exchanged into 50 mM Tris HCl pH 7.5, 50 mM NaCl, 1 mM DTT and 5% (v/v) glycerol, and concentrated to 5 mg/mL. Each compound was then added to BPL in a 10:1 molar ratio. The complex was crystallized using the hanging drop method at 4° C. in 8-12% Peg 8000 in 0.1 M Tris pH 7.5 or 8.0, and 10% (v/v) glycerol as the reservoir. A single crystal was picked using a Hampton silicon loop and streaked through cryoprotectant containing 25% (v/v) glycerol in the reservoir buffer prior to data collection. X-ray diffraction data was collected at the macromolecular crystallography beamline at the Australian Synchrotron using an ADSC Quantum 210r Detector. 90 images were collected for 1 second each at an oscillation angle of 1° for each frame. Data was integrated using HKL, and refined using the CCP4 suite of programs. PDB and cif files for the compounds were obtained using the PRODRG web interface. The models were built using cycles of manual modelling using COOT and refinement with REFMAC. The quality of the final models was evaluated using MOLPROBITY.

The X-ray structures of 4.01 and 6.09 bound to SaBPL, revealed that the 1,4-triazole linker provided limited binding to the enzyme when compared to the phosphodiester linker of biotinol-5'-AMP 2.02. The phosphodiester linker of biotinol-5'-AMP 2.02 forms a network of hydrogen bonding interactions with SaBPL (see FIG. 4). The X-ray data suggested that Triazole 6.09, could be interchanged with a phosphodiester linker to give phosphodiester 6.34

FIG. 4: Potent inhibitors of SaBPL bind in the active site of the enzyme. (4a). The crystal structure of biotinol-5' AMP 2.02 bound in the active site of SaBPL. Hydrogen bonding contacts with the amino acids of SaBPL are shown. (4b) The crystal structure of the triazole 4.01 bound in the active site of SaBPL. Hydrogen bonding contacts with the amino acids of SaBPL are shown. (4c) The backbone atoms of SaBPL from (4a) and (4b) were superimposed to reveal the remarkable overlap in the conformations of 2.02 and 4.01 (shown as a stereo diagram). (4d) The crystal structure of triazole 6.09 bound in the active site of SaBPL. Hydrogen bonding contacts with the amino acids of SaBPL are shown.

Synthesis and Screening of Triazole Analogues 4.01-4.08 Via In Situ Click Chemistry.

Preparation of triazole-based inhibitors of SaBPL via a target guided synthesis of in situ click chemistry was then carried out. The structural features of both SaBPL active site and the designed triazole 3.25 inhibitor presented the opportunity to investigate this approach. The active site of SaBPL is characterised by two distinct pockets (ATP and biotin binding pocket) which are in close proximity to each other as seen in X-ray crystal structures. More importantly, the triazole linker, as found in triazole 3.25 bound to SaBPL is positioned between the two distinct pockets of SaBPL active site.

An initial in situ click experiment was performed on the two fragments of triazole 3.25 (biotin alkyne 3.12 and adenosine azide 3.16) as shown in scheme 10. It was paramount that at least one of these fragments was capable of binding within the active site of SaBPL. Importantly, the building block biotin alkyne 3.12 was able to bind to SaBPL ($K_i=0.33\pm0.05$ μM), however, adenosine azide 3.16 had limited binding affinity to SaBPL. An in situ click experiment with adenosine 3.16 and biotin alkyne 3.12 was performed using wild type SaBPL. It was observed that wild type enzyme was ineffective at providing the in situ cycloaddition reaction at a high rate for detection by HPLC or LC-MS. Thus Arg122, which is known to act as a gatekeeper for ligands bound to SaBPL, was selectively mutated to Gly122 for use in the in situ click experiment. Using SaBPL-R122G, the cycloaddition reaction between 3.16 and 3.12 was accomplished (scheme 14).

Scheme 14:

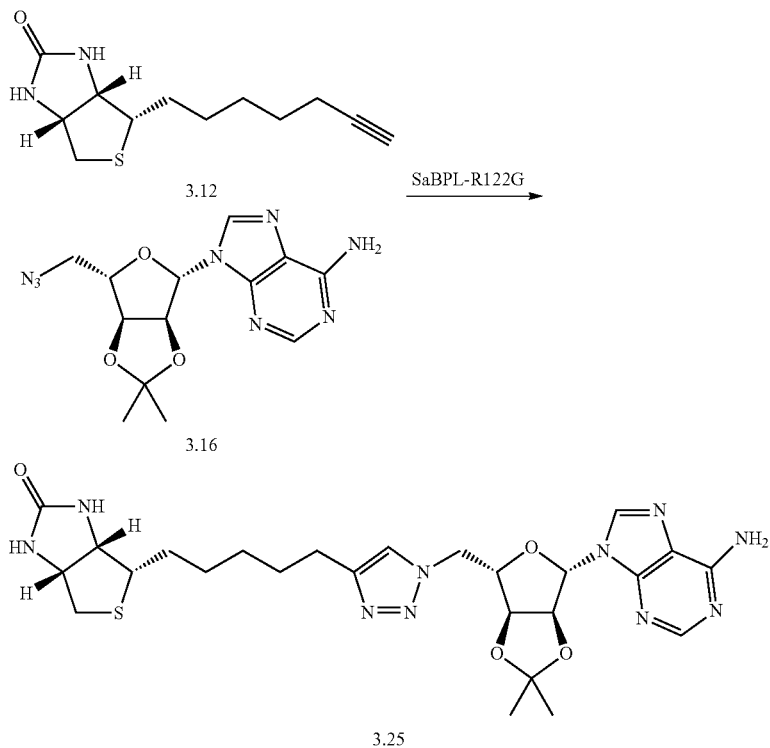

in situ click experiment with alkyne 3.12 and azide 3.16 using mutant SaBPL-R122G to give triazole 3.25 (based on HPLC).

Based on the success with in situ click chemistry to form triazole 3.25, we investigated the screening of triazole analogues 4.01-4.08 (see scheme 11). It was proposed only fragments with the appropriate tether length and with their respective azide and alkyne functional groups in close proximity to each other will undergo a 1,3-dipolar cycloaddition reaction. Fragments with their functional groups far removed from each other will not undergo the 1,3-dipolar cycloaddition reaction. In other words, SaBPL will only select and form the triazole analogues which are capable of binding within the active site.

Enzyme Inhibition and Antimicrobial Assay Results

Triazole 4.01-4.15 were assayed against SaBPL, EcBPL and HsBPL with triazole 4.01, 4.09 and 4.13 exhibiting micromolar inhibition against SaBPL as shown in table 5. The $IC_{50}$ value of each compound was determined from a dose-response curve by varying the concentration of the inhibitor under the same enzyme concentration.

TABLE 5

Inhibition of triazole 4.01, 4.09, 4.13 and 3.25 against SaBPL, HsBPL and EcBPL

| Triazole | $K_i$ (µM) SaBPL | human BPL | E. coli BPL | $IC_{50}$ (µM) SaBPL |
|---|---|---|---|---|
| 4.01 | 0.66 ± 0.15 | >90* | >90* | 4.0 ± 0.9 |

TABLE 5-continued

Inhibition of triazole 4.01, 4.09, 4.13 and 3.25 against SaBPL, HsBPL and EcBPL

| Triazole | $K_i$ (μM) SaBPL | human BPL | E. coli BPL | IC$_{50}$ (μM) SaBPL |
|---|---|---|---|---|
| 4.09 | 7.53 ± 1.90 | >10 | >10 | — |
| 4.13 | 2.86 ± 0.75 | >10 | >10 | — |
| 3.25 | 1.83 ± 0.33 | >90* | >90* | 11.6 ± 2.2 |

As shown in table 5, three triazole analogues were potent and selective against SaBPL (4.01, 4.09 and 4.13). Triazole 4.01 was the most potent of these inhibitors (Ki=0.66±0.15 uM, IC$_{50}$=4.0±0.9) and was threefold more potent than the lead triazole 3.25 ($K_i$=1.83±0.33 uM). Similar to 3.25, triazole 4.01 was found to be at least 400 fold selective towards SaBPL over EcBPL (>200 μM) and HsBPL (>200 μM).

The tether between the triazole and biotin groups of triazole 4.09 is one carbon shorter than that of triazole 3.25. This analogue was found to inhibit SaBPL with a $K_i$=7.53±1.90, which is 4 fold less potent compared to triazole 3.25 ($K_i$=1.83±0.33 uM).

Triazole 4.13, which possesses the same linker length between the adenine and biotin rings as triazole 4.01, but with the triazole ring 'shunted' towards the biotin ring was found to inhibit SaBPL with a $K_i$=2.86±0.75 μM. This is 4 fold less potent than triazole 4.01 (Ki=0.66±0.15 μM). Similar to triazole 4.01, triazole 4.13 exhibited selectivity towards SaBPL (Ki=2.86±0.75 μM) over HsBPL ($K_i$>10 μM) and EcBPL ($K_i$>10 μM).

Synthesis of Analogues

Compounds 1-6 are analogues of the lead SaBPL inhibitor BPL068. The key distinction between compound 1-6 and BPL068 involves the replacement of the 1,4-substituted 1,2,3-triazole, found in BPL068, with alternative 5 membered heterocyclic ring systems such as 1,2,4-triazole (3 and 4), 1,2,4-oxadiazole (5 and 6) and 1,3,4-oxadiazole (1 and 2).

The biotin and benzoxazolone components in compound 1-6 were remained unchanged and as found in BPL068. Whilst the tether lengths of compound 2, 4 and 6 were maintained as found in BPL068. Compounds 1, 3 and 5 contained a shorter tether length between the biotin and the 5-membered heterocyclic ring. It was postulated that the replacement the 5 membered heterocyclic 1,2,3-triazole ring of BPL068 with those found in compound 1-6 would retain or enhance the hydrogen bonding interactions with SaBPL. The interactions between SaBPL and the 1,2,3-triazole of BPL068 are Asp180, Arg122 and Arg125.

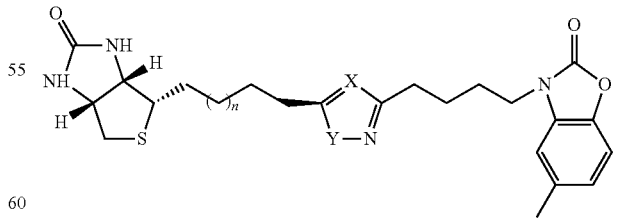

1 x = N, Y = O, n = 1
2 x = N, Y = O, n = 2
3 x = N, Y = N, n = 1
4 x = N, Y = N, n = 2
5 x = O, Y = N, n = 1
6 x = O, Y = N, n = 2

Scheme 15 shows the synthetic approach used to prepare the above compounds.
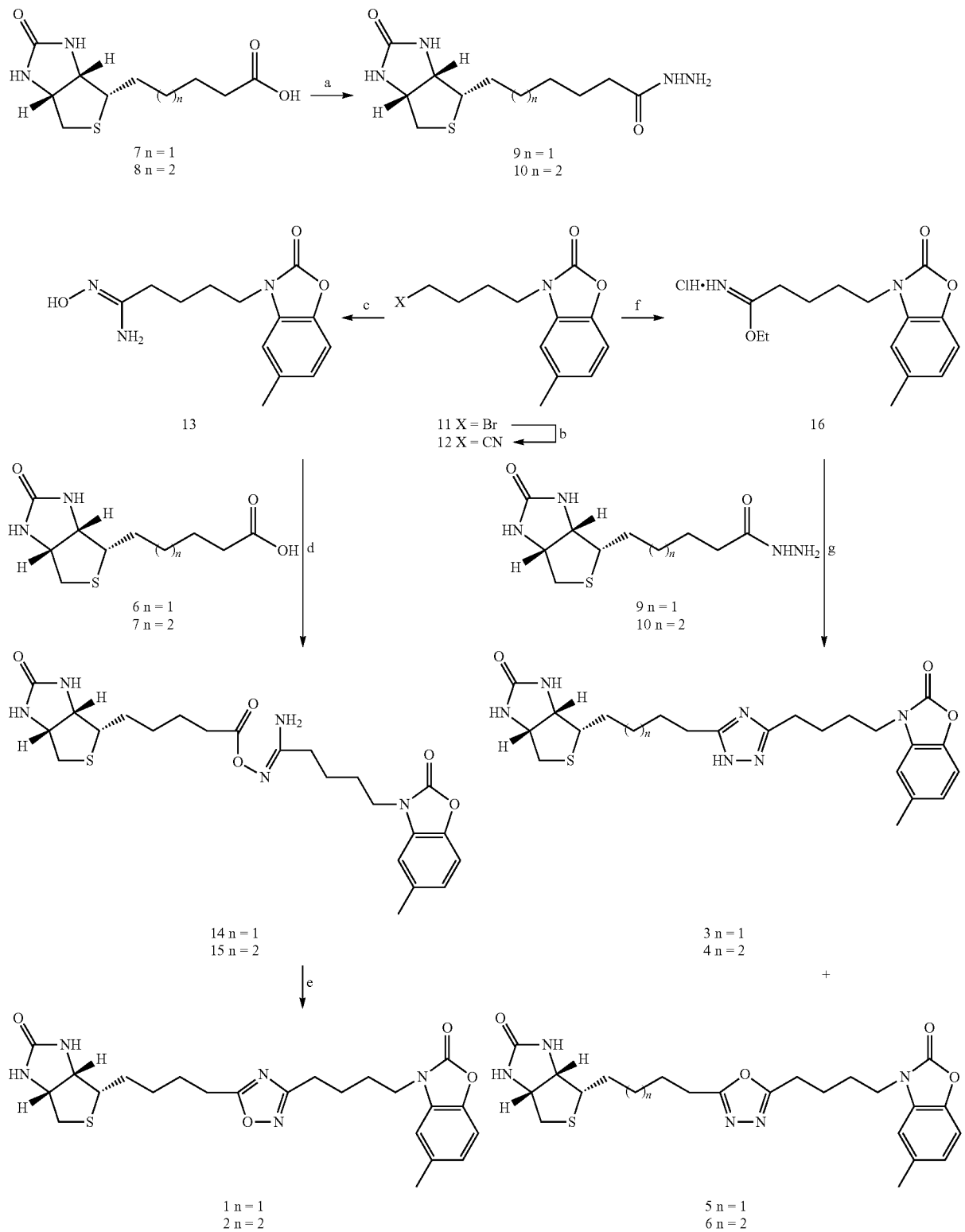
a) i) SOCl$_2$, MeOH; ii) NH$_2$NH$_2$·H$_2$O, MeOH; b) KCN, DMF, 50° C. c) NH$_2$OH, EtOH, Δ; d) EDCl, DIPEA, DMF; e) 4 Å MS, 1:1 DMF/PhMe, Δ; f) AcCl, EtOH; g) 2:1 DMF/PhMe, MW, 150° C.

| |  |  |  |  |
|---|---|---|---|---|
| Biotin (n = 1) | 1 | 3 | 5 | — |
| Purity | >95% | >95% | >95% | — |
| Rt (HPLC) min* | 17.117 | 13.772 | 16.071 | — |
| cLogP | 0.841 | 0.451 | -0.0589 | — |
| | | 1.066 | | |
| Homobiotin (n = 2) | 2 | 4 | 6 | BPL068 |
| Purity | >95% | >90% | >90% | >95% |
| Rt (HPLC) min* | 17.757 | 14.219 | 16.670 | 16.442 |
| cLogP** | 1.370 | 0.9801 | 0.470 | 1.077 |
| | | 1.595 | | |

The synthesis of compounds 1-6 is illustrated above. The synthesis of 1 and 2 was initiated by first converting the literature reported bromide 11[1] to nitrile 12 using potassium cyanide, which was then treated with hydroxylamine under basic conditions to give oxime 13. EDCl-mediated coupling between oxime 13 and biotin 7 resulted in the formation of the N-oxide ester 14. Cyclo-dehydration of 14 gave the target 1,2,4-oxadiazole 1. Similarly, EDCl-mediated coupling between oxime 13 and homobiotin 8 gave N-oxide ester 15, which upon heating under anhydrous conditions furnished 1,2,4-oxadiazole 2.

The syntheses of triazole 3 and 4 and oxadiazole 5 and 6 required access to biotin hydrazide 9[2], homobiotin hydrazide 10 and imidic ester 16. Biotin 7 and homobiotin 8 were separately esterified under acidic conditions to give their corresponding methyl esters, which upon treatment with hydrazine hydrate gave the resulting hydrazide (9 and 10). Treatment of nitrite 12 with in situ generated hydrochloride gas (acetyl chloride/ethanol) gave imidic ester 16. A mixture of 1,2,4-oxadiazole 3 and 1,2,4-triazole 5 was obtained in a single microwave reaction between imidic ester 16 and biotin hydrazide 9. Similarly, microwave reaction of homobiotin hydrazide 10 and imidic ester 16 under basic conditions gave 1,2,4-oxadiazole 5 and 1,2,4-triazole 6 in approximately a 2:1 mixture. Compounds 3-6 were isolated by silica gel chromatography.

3-[4-[5-[4-[(3aS,4S,6aR)-2-oxo-1,3,3a,4,6,6a-hexahydrothieno[3,4-d]imidazol-4-yl]butyl]-1,2,4-oxadiazol-3-yl]butyl]-5-methyl-1,3-benzoxazol-2-one (1)

A solution of compound 14 (10 mg, 0.020 mmol) containing 4 Å molecular sieves in anhydrous toluene (0.5 ml) and anhydrous DMF (0.5 ml) was stirred at reflux under a nitrogen atmosphere for 4 h. The reaction mixture was cooled and concentrated in vacuo and purified with 96:4 dichloromethane/methanol to give a white solid (5 mg, 51%)
$^1$H NMR (600 MHz, CDCl$_3$): δ 7.07 (d, J=8.4 Hz, 1H), 6.90 (d, J=8.4 Hz, 1H), 6.80 (s, 1H), 5.35 (bs, 1H), 4.67 (bs, 1H), 4.51-4.54 (m, 1H), 4.32-4.34 (m, 1H), 3.82-3.85 (m, 2H), 3.15-3.18 (m, 1H), 2.94 (dd, J=5.4, 13.2 Hz, 1H), 2.89 (t, J=7.8 Hz, 2H), 2.79-2.81 (m, 2H), 2.74 (d, J=132 Hz, 1H), 2.40 (s, 3H), 1.46-1.87 (m, 10H); $^{13}$C NMR (150 MHz, CDCl$_3$): δ 179.3, 169.8, 162.7, 154.9, 140.7, 133.8, 131.0, 122.7, 109.6, 108.9, 61.7, 60.0, 55.0, 41.7, 40.6, 27.9, 27.6, 27.1, 26.01, 25.7, 25.3, 24.0, 21.5; HPLC R$_t$=17.12 min.

3-[4-[5-[5-[(3aS,4S,6aR)-2-oxo-1,3,3a,4,6,6a-hexahydrothieno[3,4-d]imidazol-4-yl]pentyl]-1,2,4-oxadiazol-3-yl]butyl]-5-methyl-1,3-benzoxazol-2-one (2)

A solution of compound 15 (8 mg, 0.015 mmol) containing 4 Å molecular sieves in anhydrous toluene (0.5 ml) and anhydrous DMF (0.5 ml) was stirred at reflux under a nitrogen atmosphere for 4 h. The reaction mixture was cooled and concentrated in vacuo and purified with 96:4 dichloromethane/methanol to give a white gum (2 mg, 26%)
$^1$H NMR (600 MHz, CDCl$_3$): δ 7.07 (d, J=8.4 Hz, 1H), 6.90 (d, J=8.4 Hz, 1H), 6.78 (s, 1H), 4.88 (bs, 1H), 4.70 (bs, 1H), 4.52-4.54 (m, 1H), 4.32-4.34 (m, 1H), 3.82-3.85 (m, 2H), 3.14-3.18 (m, 1H), 2.93 (dd, J=5.4, 12.6 Hz, 1H), 2.85 (t, J=7.2 Hz, 2H), 2.78-2.80 (m, 2H), 2.74 (d, J=12.6 Hz, 1H), 2.40 (s, 3H), 1.39-1.87 (m, 14H); $^{13}$C NMR (150 MHz, CDCl$_3$): δ 179.6, 169.8, 162.7, 154.9, 140.7, 133.8, 131.0, 122.8, 109.6, 108.8, 62.0, 60.1, 55.3, 41.7, 40.5, 28.8, 28.5, 27.1, 26.3, 26.2, 25.3, 24.0, 21.5; LRMS: (M+Na$^+$) 508.1, expected 508.2; HPLC R$_t$: 17.76 min.

3-[4-[5-[4-[(3aS,4S,6aR)-2-Oxo-1,3,3a,4,6,6a-hexahydrothieno[3,4-d]imidazol-4-yl]butyl]-1H-1,2,4-triazol-3-yl]butyl]-5-methyl-1,3-benzoxazol-2-one (3)

and

3-[4-[5-[4-[(3aS,4S,6aR)-2-oxo-1,3,3a,4,6,6a-hexahydrothieno[3,4-d]imidazol-4-yl]butyl]-1,3,4-oxadiazol-2-yl]butyl]-5-methyl-1,3-benzoxazol-2-one (5)

To a suspension of biotin hydrazide 9$^2$ (28 mg, 0.108 mmol) in anhydrous DMF (0.5 ml) were added imidic ester 16 (32 mg, 0.102 mmol), DIPEA (52 mg, 0.410 mmol) and anhydrous toluene (0.5 ml). The mixture was stirred and microwaved at 150° C. for 2 h (with variable pressure and power), concentrated in vacuo and purified by silica gel chromatography eluting with 5% methanol in dichloromethane to give 1,2,4-oxadiazole 5 (16 mg, 33%) and eluting at 12% methanol in dichloromethane to give 1,2,4-triazole 3 (7 mg, 15%)

1,2,4-Oxadiazole (5): $^1$H NMR (600 MHz, CDCl$_3$): δ 7.08 (d, J=7.8 Hz, 1H), 6.91 (d, J=7.8 Hz, 1H), 6.79 (s, 1H), 5.42 (bs, 1H), 4.84 (bs, 1H), 4.51-4.54 (m, 1H), 4.32-4.34 (m, 1H), 3.85 (t, J=6.6 Hz, 2H), 3.15-3.18 (m, 1H), 2.93 (dd, J=5.4, 12.6 Hz, 1H), 2.90 (t, J=7.2 Hz, 2H), 2.84 (t, J=7.8 Hz, 2H), 2.74 (d, J=12.6 Hz, 1H), 2.72 (s, 3H), 1.50-1.90 (m, 10H); $^{13}$C NMR (150 MHz, CDCl$_3$): δ 166.8, 166.2, 163.0, 154.9, 140.7, 133.9, 130.9, 122.9, 109.7, 108.8, 61.8, 60.1, 55.2, 41.5, 40.5, 28.1, 28.0, 27.0, 26.2, 24.8, 25.7, 23.4, 21.5; LRMS (M+Na$^+$): 494.2 expected 494.2 HPLC R$_t$: 16.07 min 1,2,4-triazole (3): $^1$H NMR (600 MHz, CDCl$_3$): δ 13:26 (bs, 1H), 7.53 (bs, 1H), 7.06 (d, J=7.8 Hz, 1H), 6.89 (d, J=7.8 Hz, 1H), 6.78 (s, 1H), 6.54 (bs, 1H), 4.56-4.58 (m, 1H), 4.41-4.43 (m, 1H), 3.83 (t, J=6.6 Hz, 2H), 3.00-3.17 (m, 1H), 2.96 (dd, J=6.6, 12.0 Hz, 1H), 2.71-2.86 (m, 5H), 1.60-1.88 (m, 6H), 1.27-1.45 (m, 4H); $^{13}$C NMR (150 MHz, CDCl$_3$): δ 165.1, 155.0, 140.7, 133.8, 131.0, 122.7, 109.6, 108.9, 61.7, 60.2, 59.9, 41.9, 41.0, 29.7, 28.2, 27.9, 27.7, 27.2, 27.0, 25.2, 21.5; LRMS: (M+H$^+$): 471.1 expected 471.2; HPLC R$_t$: 13.77 min.

3-[4-[5-[5-[(3aS,4S,6aR)-2-oxo-1,3,3a,4,6,6a-hexahydrothieno[3,4-d]imidazol-4-yl]pentyl]-1H-1,2,4-triazol-3-yl]butyl]-5-methyl-1,3-benzoxazol-2-one (4)

and

3-[4-[5-[5-[(3aS,4S,6aR)-2-oxo-1,3,3a,4,6,6a-hexahydrothieno[3,4-d]imidazol-4-yl]pentyl]-1,3,4-oxadiazol-2-yl]butyl]-6-methyl-1,3-benzoxazol-2-one (6)

To a suspension of homobiotin hydrazide 10 (30 mg, 0.110 mmol) in DMF (0.5 ml) were added imidic ester 16 (36 mg, 0.115 mmol), DIPEA (58 mg, 0.464 mmol) and toluene (0.25 ml). The mixture was stirred and microwaved at 150° C. for 2 h (with variable pressure and power), concentrated in vacuo and purified by silica gel chromatography eluting at 5% methanol in dichloromethane to give 1,2,4-oxadiazole 6 (17 mg, 32%) and eluting at 10% methanol in dichloromethane to give 1,2,4-triazole 4 (10 mg, 18%)

1,2,4-Oxadiazole (6): $^1$H NMR (600 MHz, CDCl$_3$): δ 7.08 (d, J=8.4 Hz, 1H), 6.91 (d, J=8.4 Hz, 1H), 5.79 (bs, 1H), 5.24 (bs, 1H), 4.50-4.53 (m, 1H), 4.30-4.33 (m, 1H), 3.84-3.86 (m, 2H), 3.14-3.17 (m, 1H), 2.85-2.93 (m, 3H), 2.73-2.83 (m, 3H), 1.44-1.89 (m, 14H); $^{13}$C NMR (150 MHz, CDCl$_3$): δ 167.0, 166.1, 163.4, 154.9, 140.7, 133.9, 130.9, 122.8, 109.7, 108.8, 62.0, 60.1, 55.7, 41.5, 40.5, 28.9, 28.5, 28.4, 27.0, 25.9, 25.2, 24.7, 23.4, 21.5; LRMS: (M+Na$^+$): 508.1 expected 508.2; HPLC R$_t$: 16.67 min.

1,2,4-triazole (4): $^1$H NMR (600 MHz, CDCl$_3$): δ 13.75 (bs, 1H), 7.86 (bs, 1H), 7.05 (d, J=8.4 Hz, 1H), 6.88 (d, J=8.4 Hz, 1H), 6.78 (s, 1H), 6.37 (bs, 1H), 4.60-4.61 (m, 1H), 4.35 (dd, J=3.6, 7.2 Hz, 1H), 3.78-3.86 (m, 2H), 3.15-3.18 (m, 1H), 2.93-2.97 (m, 2H), 2.74-2.79 (m, 4H), 2.39 (s, 3H), 1.35-1.84 (m, 14H); $^{13}$C NMR (150 MHz, CDCl$_3$): δ 165.2, 162.8, 154.9, 140.6, 133.8, 131.0, 122.7, 109.5, 108.9, 61.2, 60.6, 55.2, 41.9, 40.8, 28.2, 28.1, 27.8, 27.3, 27.1, 26.3, 25.2, 21.5 LRMS: (M+Na$^+$): 507.2 expected 507.2; HPLC R$_t$=14.21 min.

6-[(3aS,4S,6aR)-2-Oxo-1,3,3a,4,6,6a-hexahydrothieno[3,4-d]imidazol-4-yl]hexanehydrazide (10)

To a suspension of homobiotin 8 (150 mg, 0.58 mmol) in dry methanol (1.5 ml) was added drop-wise thionyl chloride (276 mg, 169 μL, 2.32 mmol) and stirred under a nitrogen atmosphere for 2 h. The mixture was concentrated in vacuo, suspended in methanol (2 ml) and was added hydrazine hydrate (0.5 ml) and stirred for 16 h. The reaction mixture was concentrated in vacuo, dissolved in water (5 ml) and washed with chloroform (2×5 ml). The aqueous layer was concentrated in vacuo to give a white powder (121 mg, 77%).

$^1$H NMR (300 MHz, D$_2$O): δ 4.59 (dd, J=7.8, 4.5 Hz, 1H), 4.41 (dd, J=7.8, 4.5 Hz, 1H), δ 2.98 (dd, J=13.2, 4.9 Hz, 1H), 2.76 (d, J=13.2 Hz, 1H), 2.19-2.24 (m, 2H), 1.24-1.77 (m, 8H); $^{13}$C NMR (75 MHz, D$_2$O): δ 176.4, 166.0, 62.8, 60.9, 56.1, 40.3, 34.1, 28.7, 28.6, 28.4, 25.4.

5-(5-methyl-2-oxo-1,3-benzoxazol-3-yl)pentanenitrile (12)

A solution of bromide 11$^1$ (500 mg, 1.77 mmol), potassium cyanide (126 mg, 1.94 mmol) in anhydrous DMF (5 ml) was stirred at 50° C. under a nitrogen atmosphere for 8 h. The reaction mixture was cooled to room temperature and diluted with dichloromethane (50 ml) and washed with water (50 ml) and brine (50 ml). The organic layer was dried over sodium sulphate, filtered and concentrated in vacuo. The residue was purified by silica gel chromatography eluting with 3:2 ethylacetate/hexane mixture to give an off white solid (289 mg, 71%).

$^1$H NMR (300 MHz, CDCl$_3$): δ 7.05 (d, J=7.8 Hz, 1H), 6.90 (d, J=7.8 Hz, 1H), 6.78 (s, 1H), 3.84 (t, J=6.9 Hz, 2H), 2.44 (t, J=6.9 Hz, 2H), 2.38 (s, 3H), 1.89-1.99 (m, 2H), 1.69-1.78 (m, 2H); $^{13}$C NMR (75 MHz, CDCl$_3$): δ 154.9, 140.6, 134.0, 130.7, 123.0, 119.2, 109.7, 108.8, 41.0, 26.8, 22.4, 21.6, 16.7.

N'-hydroxy-5-(5-methyl-2-oxo-1,3-benzoxazol-3-yl)pentanamidine (13)

A solution of hydroxylamine hydrochloride salt (345 mg, 5.00 mmol) and phenolphthalein (1 crystal) in anhydrous methanol (5 ml) was stirred at reflux under an nitrogen atmosphere. Sodium methoxide was added portion-wise until a pink solution persisted (approximately 350 mg was used). The hot solution was filtered directly into a solution of compound 2 (115 mg, 0.50 mmol) in anhydrous ethanol (5 ml). The reaction mixture was stirred at reflux under a nitrogen atmosphere for 6 h. The reaction mixture was cooled, concentrated in vacuo and purified by silica gel chromatography eluting with 19:1 dichloromethane/methanol to give a brown solid (68 mg, 52%).

$^1$H NMR (300 MHz, CDCl$_3$): δ 7.00 (d, J=8.1 Hz, 1H), 6.82-6.88 (m, 1H), 6.76-6.76 (m, 1H), 4.85 (bs, 1H), 3.76 (t, J=6.9 Hz, 2H), 3.61 (bs, 2H), 2.32 (s, 3H), 2.11 (t, J=7.5 Hz, 2H), 1.69-1.79 (m, 2H), 1.51-1.61 (m, 2H); $^{13}$C NMR (75 MHz, CDCl$_3$) δ 177.7, 140.9, 134.4, 131.0, 123.3, 109.9, 109.3, 100.3, 41.7, 30.5, 27.1, 24.0, 21.7; LRMS (M+H$^+$): 264.1 expected 264.1.

[(Z)-[1-amino-5-(5-methyl-2-oxo-1,3-benzoxazol-3-yl)pentylidene]amino] 5-[(3aS,4S,6aR)-2-oxo-1,3,3a,4,6,6a-hexahydrothieno[3,4-d]imidazol-4-yl]pentanoate (14)

To a suspension of biotin 7 (23 mg, 0.092 mmol) and compound 13 (22 mg, 0.083 mmol) in anhydrous DMF (0.5 ml) was added EDCl (16 mg, 0.10 mmol) and DIPEA (13 mg, 0.10 mmol) and stirred under a nitrogen atmosphere at ambient temperature for 12 h. The reaction mixture was diluted with dichloromethane (25 ml) and washed with water (25 ml) and brine (25 ml). The organic layer was dried over sodium sulphate, filtered and concentrated in vacuo. The residue was purified by silica gel chromatography eluting with 19:1 dichloromethane/methanol to give a yellow oil (21 mg, 51%).

$^1$H NMR (600 MHz, CDCl$_3$): δ 7.08 (d, J=8.4 Hz, 1H), 6.91 (d, J=8.4 Hz, 1H), 6.80 (s, 1H), 5.60 (bs, 1H), 5.04 (m, 3H), 4.50-4.51 (m, 1H), 4.30-4.32 (m, 1H), 3.85 (t, J=6.6 Hz, 2H), 3.14-3.17 (m, 1H), 2.91 (dd, J=5.4, 13.2 Hz, 1H), 2.73 (d, J=13.3 Hz, 1H), 2.42 (t, J=7.8 Hz, 2H), 2.40 (s, 3H), 2.34 (t, J=7.8 Hz, 2H), 1.47-1.86 (m, 10H); $^{13}$C NMR (150 MHz, CDCl$_3$): δ 171.0, 163.3, 158.0, 155.4, 140.7, 134.1, 130.7, 123.0, 109.7, 109.0, 61.8, 60.1, 55.3, 41.0, 40.5, 32.7, 30.1, 28.2, 28.1, 26.8, 24.9, 23.7, 21.5

[(Z)-[1-amino-5-(5-methyl-2-oxo-1,3-benzoxazol-3-yl)pentylidene]amino] 6-[(3aS,4S,6aR)-2-oxo-1,3,3a,4,6,6a-hexahydrothieno[3,4-d]imidazol-4-yl]hexanoate (15)

To a suspension of homobiotin 8$^3$ (10 mg, 0.039 mmol) and compound 13 (11 mg, 0.043 mmol) in anhydrous DMF (0.5 ml) was added EDCl (7 mg, 0.047 mmol) and DIPEA (6 mg, 0.045 mmol) and stirred under a nitrogen atmosphere at ambient temperature for 12 h. The reaction mixture was diluted with dichloromethane (25 ml) and washed with water (25 ml) and brine (25 ml). The organic layer was dried over sodium sulphate, filtered and concentrated in vacuo. The residue was purified by silica gel chromatography eluting with 19:1 dichloromethane/methanol to give a yellow oil (18 mg, 46%).

$^1$H NMR (600 MHz, CDCl$_3$): δ 7.08 (d, J=7.2 Hz, 1H), 6.91 (d, J=7.2 Hz, 1H), 6.80 (s, 1H), 5.38 (bs, 1H), 4.99 (bs, 2H), 4.60 (bs, 1H), 4.49-4.52 (m, 1H), 4.29-4.32 (m, 1H), 3.82-3.87 (m, 2H), 3.13-3.17 (m, 1H), 2.91 (dd, J=4.8, 12.6 Hz, 1H), 2.73 (d, J=12.6 Hz, 1H), 2.40 (s, 3H), 2.32-2.38 (m, 2H), 2.12 (t, J=7.2 Hz, 2H), 1.40-1.86 (m, 12H); LRMS (M+Na$^+$): 526.2 expected 526.2.

5-(5-methyl-2-oxo-1,3-benzoxazol-3-yl)pentanimidate hydrochloride (16)

To a solution of nitrile 11 (100 mg, 0.43 mmol) in dry ethanol (0.5 ml) was added acetic acid (0.5 ml) and the solution was stirred in a sealed round bottom flask for 6 h. The reaction mixture was concentrated in vacuo to give a white solid (135 mg, 100%).

$^1$H NMR: 7.02 (d, J=8.1 Hz, 1H), 6.86 (d, J=8.1 Hz, 1H), 6.80 (s, 1H), 4.42 (q, J=6.3 Hz, 2H), 3.78-3.81 (m, 2H), 2.63 (t, J=6.9 Hz, 2H), 2.34 (s, 3H), 1.68-1.86 (m, 4H), 1.39 (t, J=6.6 Hz, 3H); LRMS (M+H$^+$): 277.1 expected 277.2

2

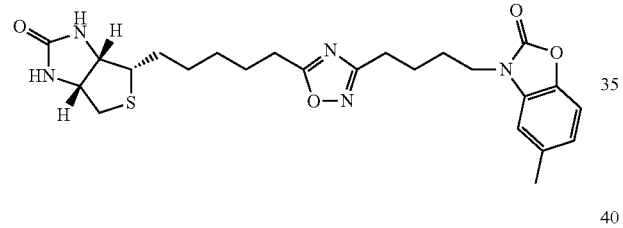

The above compound, 3-[4-[5-[5-[(3aS,4S,6aR)-2-oxo-1,3,3a,4,6,6a-hexahydrothieno[3,4-d]imidazol-4-yl]pentyl]-1,2,4-oxadiazol-3-yl]butyl]-5-methyl-1,3-benzoxazol-2-one (2), was shown to have inhibitory activity against the BPLs from both *Staphylococcus aureus* and *Mycobacteria tuberculosis*, $K_i$ *S. aureus* BPL=2.2±0.8 µM, $K_i$ *M. tuberculosis* BPL=290±16 µM Although the invention has been herein shown and described in what is conceived to be the most practical and preferred embodiments, it is recognized that departures can be made within the scope of the invention, which is not to be limited to the details described herein but it is to be accorded the full scope of the appended claims so as to embrace any and all equivalent structures and applications.

The claims defining the invention are as follows:

1. A compound of formula (I)

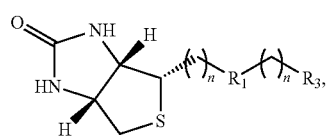

(I)

wherein n is an integer from 1 to 10;

$R_1$ is selected from the group consisting of:

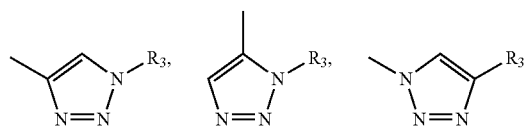

imidazole,

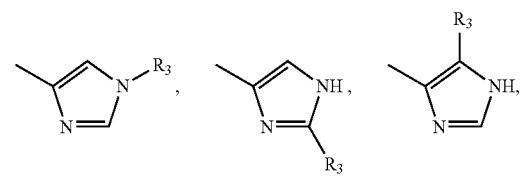

pyrazole,

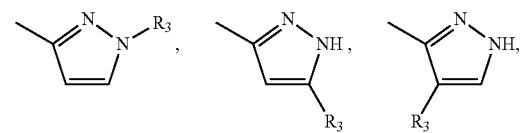

pyrrole,

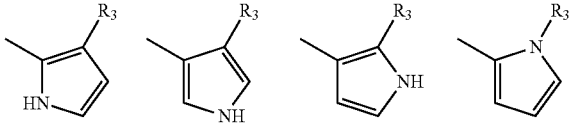

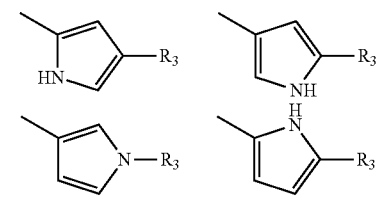

thiophene,

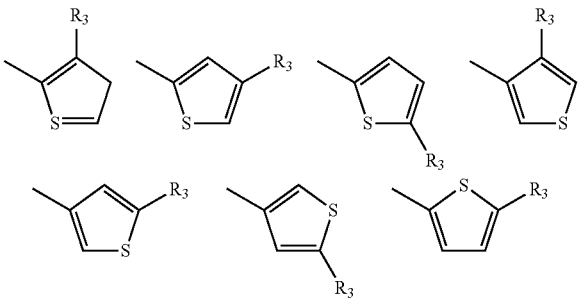

tetrazole,

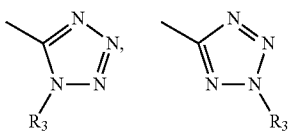

oxazole,

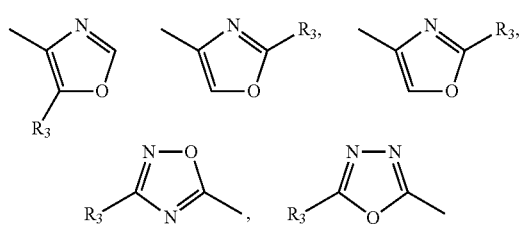

triazole

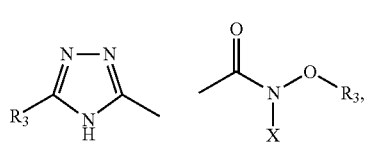

where X is selected from H or OH,

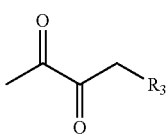

phosphodiester,

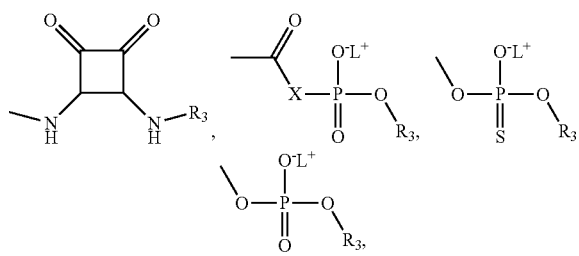

where L is selected from $Na^+$, $K^+$; X is selected from $CH_2$, $CF_2$, NH,
$R_3$ is selected from the group consisting of:
  H, $C_1$-$C_{10}$ alkyl, $C_1$-$C_{10}$ alkenyl, $C_1$-$C_{10}$ alkynyl;
  a nucleoside selected from the group consisting of adenosine, cytidine, uridine, guanosine, thymidine, inosine,
  adenine, guanine, thymine, uracil, and cytosine;
  benzoxazolone, benzoxazole, benzofuran, benzimidazole,

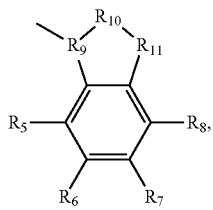

where:
  $R_5$, $R_6$, $R_7$, $R_8$ are selected from the group consisting of H, $C_1$-$C_5$ alkyl, halogen, $NH_2$, OH, $NR_{12}R_{13}$, SH, $SR_{13}$:
    where $R_{12}$ and $R_{13}$ are selected from the group consisting of H, $C_1$-$C_5$ alkyl;
  $R_9$ is selected from the group consisting of N, NH;
  $R_{10}$ is selected from the group consisting of $CH_2$, C=O, C=N—R;
  $R_{11}$ is selected from the group consisting of N, NH, O, S;
napthyl,

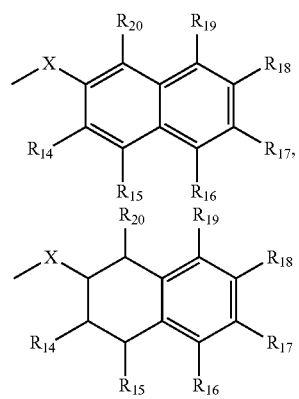

where:
  X is selected from the group consisting of O, $NR_{12}R_{13}$, $SR_{13}$;
  $R_{14}$, $R_{15}$, $R_{16}$, $R_{17}$, $R_{18}$, $R_{19}$, $R_{20}$ are selected from the group consisting of H, $C_1$-$C_5$ alkyl, halogen, $NH_2$, OH, $NR_{12}R_{13}$, SH, $SR_{13}$:
    where $R_{12}$ and $R_{13}$ are selected from the group consisting of H, $C_1$-$C_5$ alkyl.

2. A pharmaceutical composition comprising as an active ingredient at least one compound of formula (I) as claimed in claim 1, optionally together with one or more pharmacologically acceptable excipients.

3. A method of treating bacterial infection, fungal infection, or protozoan infection via administration of at least one compound of claim 1 in a patient in need thereof.

4. A method of treating bacterial infection, fungal infection, or protozoan infection via administration of the pharmaceutical composition of claim 2 in a patient in need thereof.

5. The method of claim 4, wherein the bacterial infection is a *Staphylococcus aureus* infection.

6. The method of claim 4, wherein the bacterial infection is a *Mycobacteria tuberculosis* infection.

* * * * *